United States Patent [19]
Kohno et al.

[11] Patent Number: 6,071,245
[45] Date of Patent: Jun. 6, 2000

[54] DIAGNOSTIC AGENT FOR LIVER FUNCTION

[75] Inventors: Tadashi Kohno, Kanagawa; Isaburo Hosoi, Saitama; Junko Ohshima; Asuka Ito, both of Kanagawa; Kunihiko Shibata, Chiba, all of Japan

[73] Assignee: Tokyo Gas Company Limited, Tokyo, Japan

[21] Appl. No.: 09/164,710

[22] Filed: Oct. 1, 1998

[30] Foreign Application Priority Data

| Oct. 6, 1997 | [JP] | Japan | 9-272558 |
| Oct. 6, 1997 | [JP] | Japan | 9-272737 |
| Oct. 6, 1997 | [JP] | Japan | 9-272889 |
| Oct. 21, 1997 | [JP] | Japan | 9-288660 |
| Dec. 11, 1997 | [JP] | Japan | 9-341262 |
| Jan. 16, 1998 | [JP] | Japan | 10-006411 |
| Feb. 5, 1998 | [JP] | Japan | 10-024733 |

[51] Int. Cl.$^7$ ............................................ A61B 5/08
[52] U.S. Cl. ........................ 600/532; 600/573; 600/584
[58] Field of Search ............................. 600/532, 573, 600/584, 543; 128/898

[56] References Cited

U.S. PATENT DOCUMENTS

| 5,386,832 | 2/1995 | Wagner et al. |
| 5,715,835 | 2/1998 | Lishko et al. ............................ 128/898 |

FOREIGN PATENT DOCUMENTS

| 0733374 | 9/1996 | European Pat. Off. ....... A61K 51/04 |
| 0826377 | 3/1998 | European Pat. Off. ....... A61K 49/00 |
| WO9118105 | 11/1991 | WIPO ............................... C12P 7/62 |
| WO9201937 | 2/1992 | WIPO ............................ G01N 33/60 |

OTHER PUBLICATIONS

"Breath tests: concepts, applications and limitations," D. Rating et al., Eur J Pediatr (1997) 156 [Suppl 1]: S18–S23.

"Test for Alcoholic Cirrhosis by Conversion of [$^{14}$C]–or [$^{13}$C]Galactose To Expired $CO_2$" Walton W. Shreeve, M.D., et al., vol. 71, No. 1, Gastroenterology 71:96–101, 1976.

"In Vivo Oxidation of [$^{13}$C]Galactose in Patients with Galactose–1–Phosphate Uridyltrasferase Deficiency," Gerard T. Berry et al., Biochemical and Molecular Medicine 56, 158–165 (1995).

Mion F. et al.: Life Sciences 1994; 54: 2093–2098.

Walton W. et al.: Gastroenterology 1976; 71: 98–101.

Xiaoming Z. et al.: Zhonghua Heyixue Zazhi 1987; 7: 90–92.

Watkins J. B. et al.: Gastroenterology 1982; 82: 911–917.

Mullen K. D. et al.: Hepatology 1986; 6: 622–630.

Xinhua Z. et al.: Zhonghua Heyixue Zazhi 1993; 13: 164–166.

*Primary Examiner*—Cary O'Connor
*Assistant Examiner*—Ryan Carter
*Attorney, Agent, or Firm*—Davidson, Davidson & Kappel, LLC

[57] ABSTRACT

The present invention relates to a diagnostic agent for liver function, comprising a compound labelled with $^{13}$C at least at one specific position selected from the group consisting of the following (a) to (f):

(a) galactose, glucose or xylose labelled with $^{13}$C at least at one specific position or a starch composed of glucose units labelled with $^{13}$C at least at one specific position;

(b) a polar amino acid, heterocyclic amino acid, isoleucine or valine labelled with $^{13}$C at least at one specific position;

(c) a carboxylic acid constituting the glycolytic pathway or the citric acid cycle, labelled with $^{13}$C at least at one specific position;

(d) a fatty acid labelled with $^{13}$C at least at one specific position;

(e) a glyceride labelled with $^{13}$C at least at one specific position; and (f) glycerol labelled with $^{13}$C at least at one specific position.

According to the present invention, a diagnostic agent for liver function which imposes less physical burden on a subject, can give accurate test result immediately, and can be used safely without side effects is provided. The diagnostic agent of the invention is useful for evaluating the liver function of a subject at the time when the test is carried out.

12 Claims, 25 Drawing Sheets

Schematic Diagram of Method for Recovering Exhalation from Rat

A rat anesthetized by intraperitoneal administration of Nembutal is fixed on its back. The head is covered with a cylindrical cap. A test sample is administered from the femoral vein. The exhalation is sucked with a stroke pump and introduced directly into a $^{13}CO_2$ analyzer. A Perma Pure Drier is located in the passage to remove moisture in the exhalation.

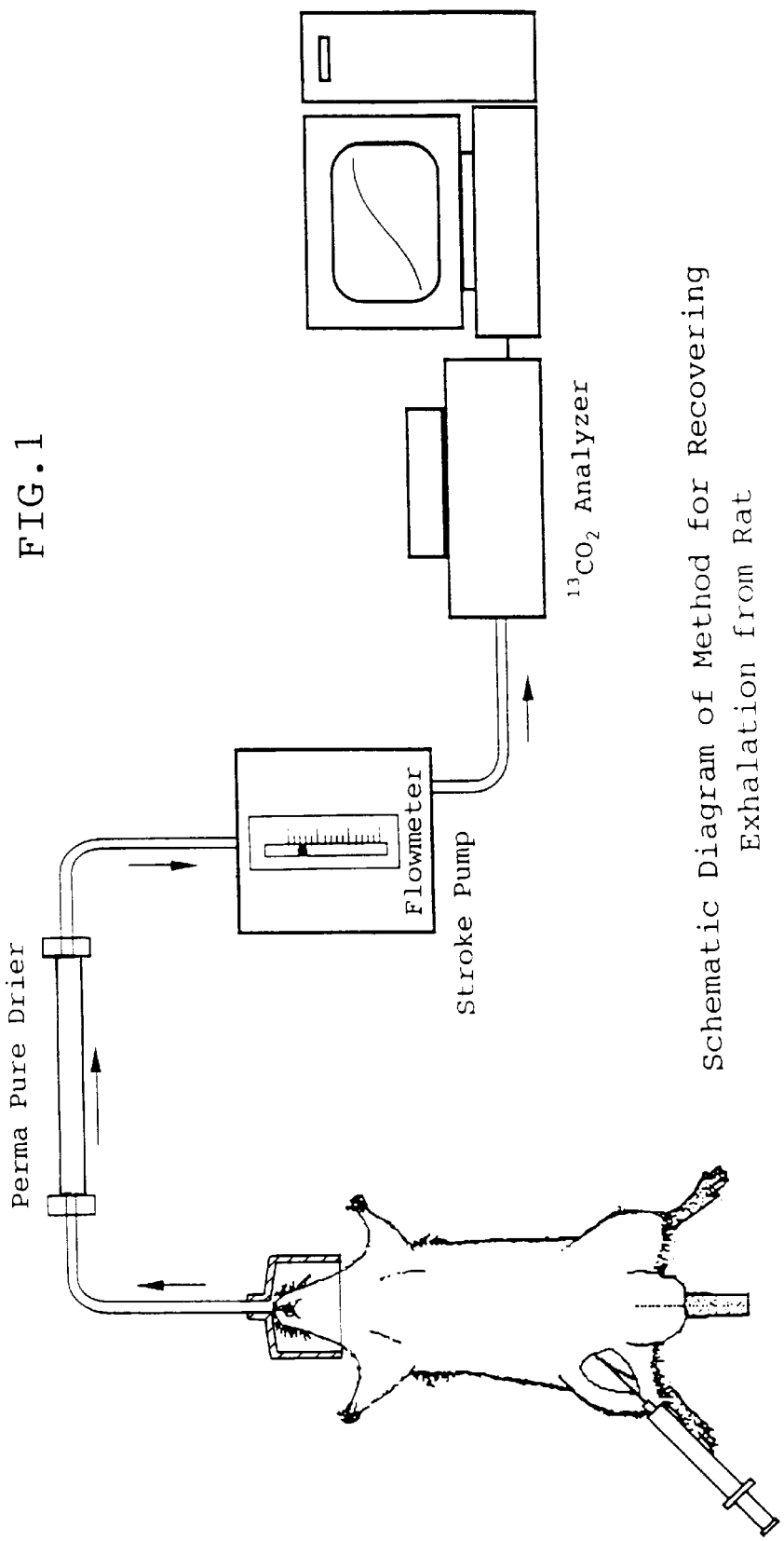

FIG.2

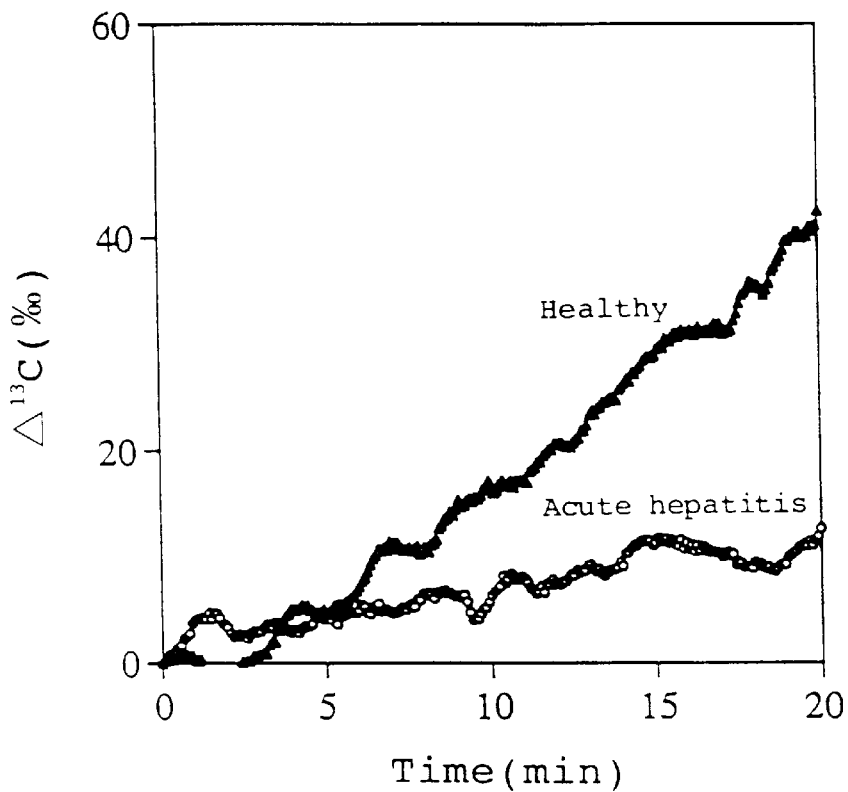

Increase of $^{13}CO_2$ in Exhalation
after Administration of 1-$^{13}$C-Galactose 1-$^{13}$C-galactose (100 mg/kg) was administered intravenously to healthy rats (male SD; 8-week old; total bilirubin value $\leq$ 0.5 mg/dl; n=3) and rats with acute hepatitis (male SD; 8-week old; total bilirubin value $\geq$ 2.8 mg/dl; n=3) at time 0. Then, degrees of increase of $^{13}$C levels in exhaled $CO_2$ ($\Delta^{13}C$ (‰)) were measured. All the rats were fasted overnight before the experiment.

FIG. 3

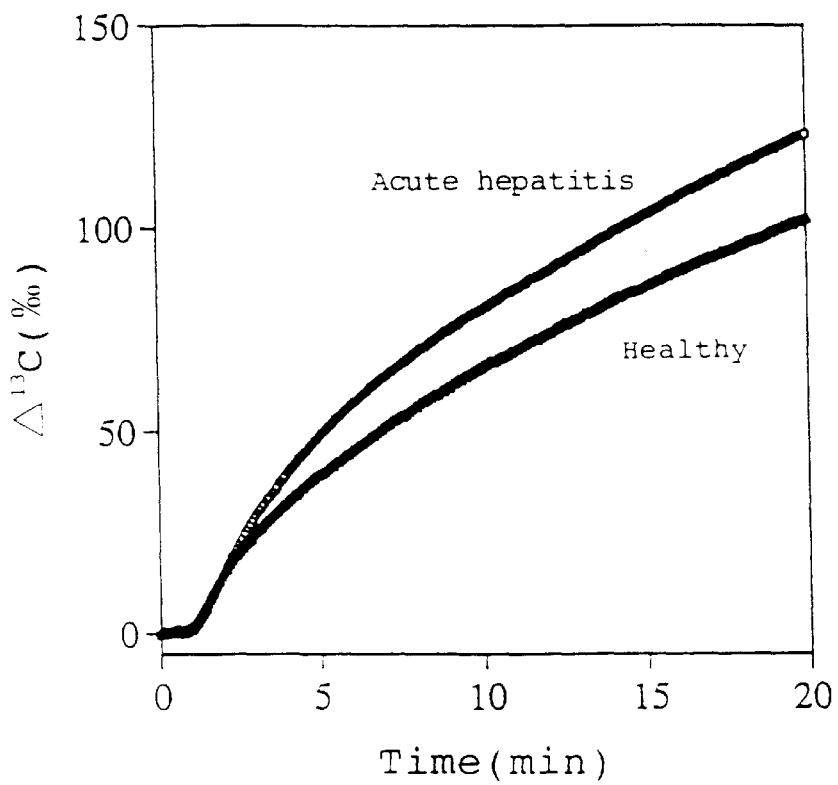

Increase of $^{13}CO_2$ in Exhalation
after Administration of 1-$^{13}$C-Glucose 1-$^{13}$C-glucose (100 mg/kg) was administered intravenously to healthy rats (male SD; 8-week old; total bilirubin value ≦ 0.6 mg/dl; n=4) and rats with acute hepatitis (male SD; 8-week old; total bilirubin value > 3 mg/dl; n=4) at time 0. Then, degrees of increase of $^{13}$C levels in exhaled $CO_2$ ($\Delta^{13}C$ (‰)) were measured. All the rats were fasted overnight before the experiment.

FIG. 4

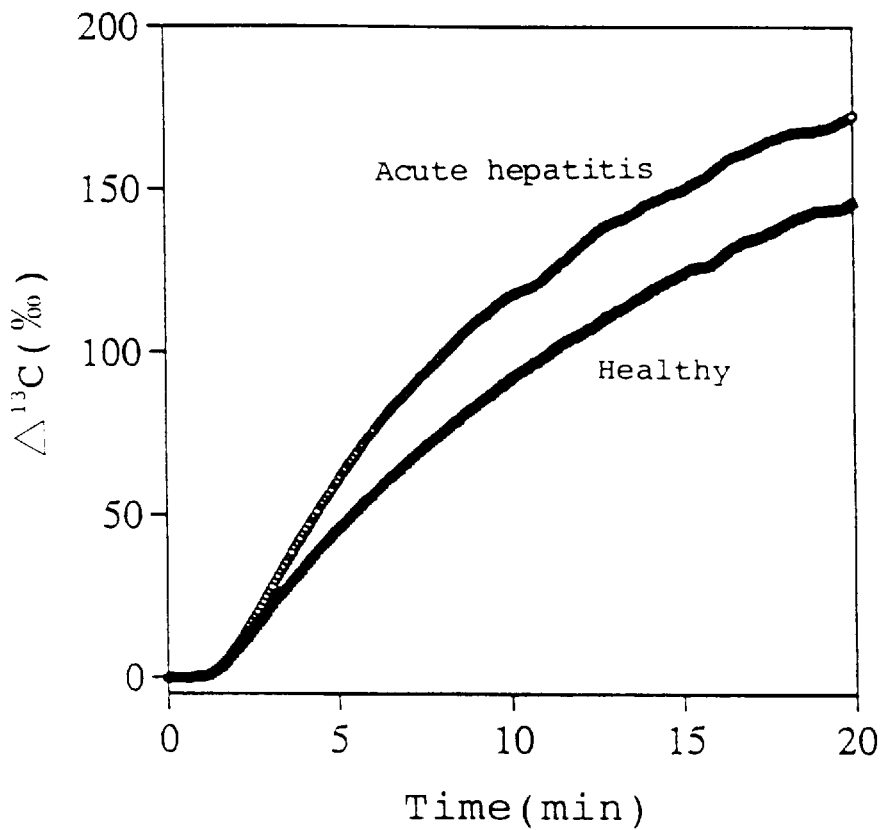

Increase of $^{13}CO_2$ in Exhalation
after Administration of $3-^{13}C$-Glucose $3-^{13}C$-glucose (100 mg/kg) was administered intravenously to healthy rats (male SD; 8-week old; total bilirubin value $\leq 0.6$ mg/dl; n=4) and rats with acute hepatitis (male SD; 8-week old; total bilirubin value $\geq 2.1$ mg/dl; n=4) at time 0. Then, degrees of increase of $^{13}C$ levels in exhaled $CO_2$ ($\Delta^{13}C$ (‰)) were measured. All the rats were fasted overnight before the experiment.

FIG. 5

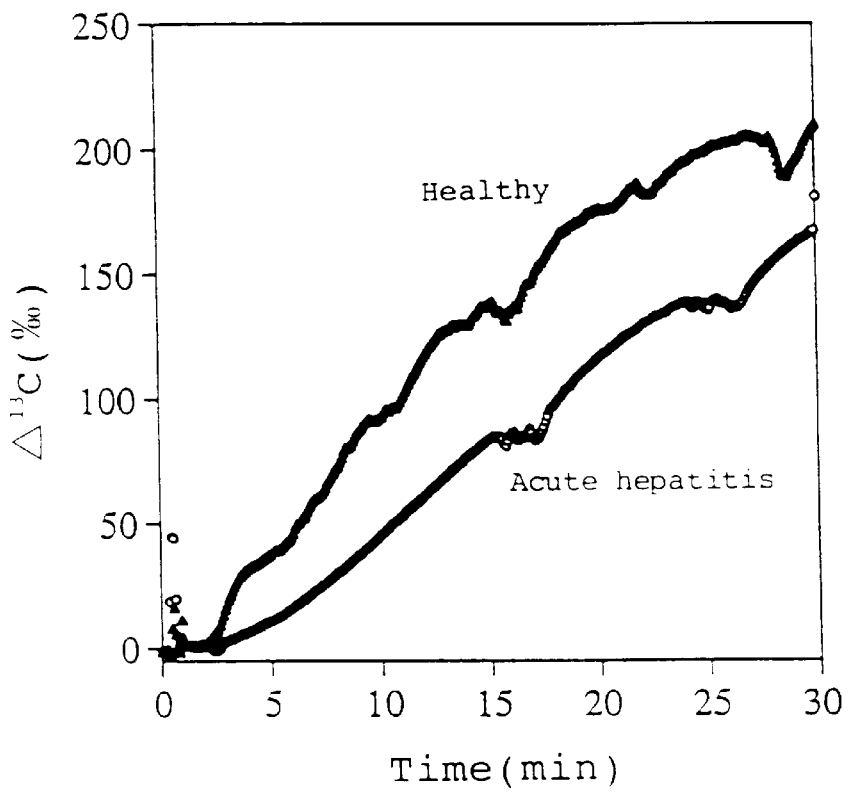

Increase of $^{13}CO_2$ in Exhalation
after Administration of U-$^{13}$C-Starch

U-$^{13}$C-starch (30 mg/kg) was administered orally to
healthy rats (male SD; 8-week old; total bilirubin value =
0.4 mg/dl; n=4) and rats with acute hepatitis (male SD; 8-
week old; total bilirubin value > 3 mg/dl; n=4) at time 0.
Then, degrees of increase of $^{13}$C levels in exhaled $CO_2$ ($\Delta^{13}$C
(‰)) were measured. All the rats were fasted overnight
before the experiment.

FIG. 6

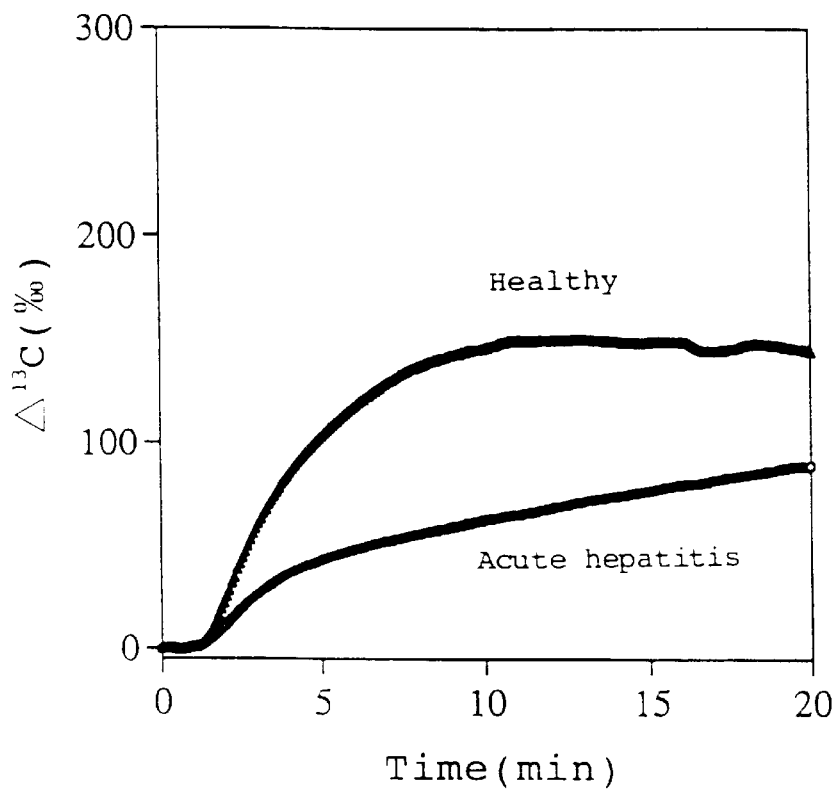

Increase of $^{13}CO_2$ in Exhalation
after Administration of $1\text{-}^{13}C\text{-Arginine}$ $1\text{-}^{13}C$-arginine (50 mg/kg) was administered intravenously to healthy rats (male SD; 8-week old; total bilirubin value $\leq 0.5$ mg/dl; n=4) and rats with acute hepatitis (male SD; 8-week old; total bilirubin value > 3 mg/dl; n=4) at time 0. Then, degrees of increase of $^{13}C$ levels in exhaled $CO_2$ ($\Delta^{13}C$ (‰)) were measured. All the rats were fasted overnight before the experiment.

FIG. 7

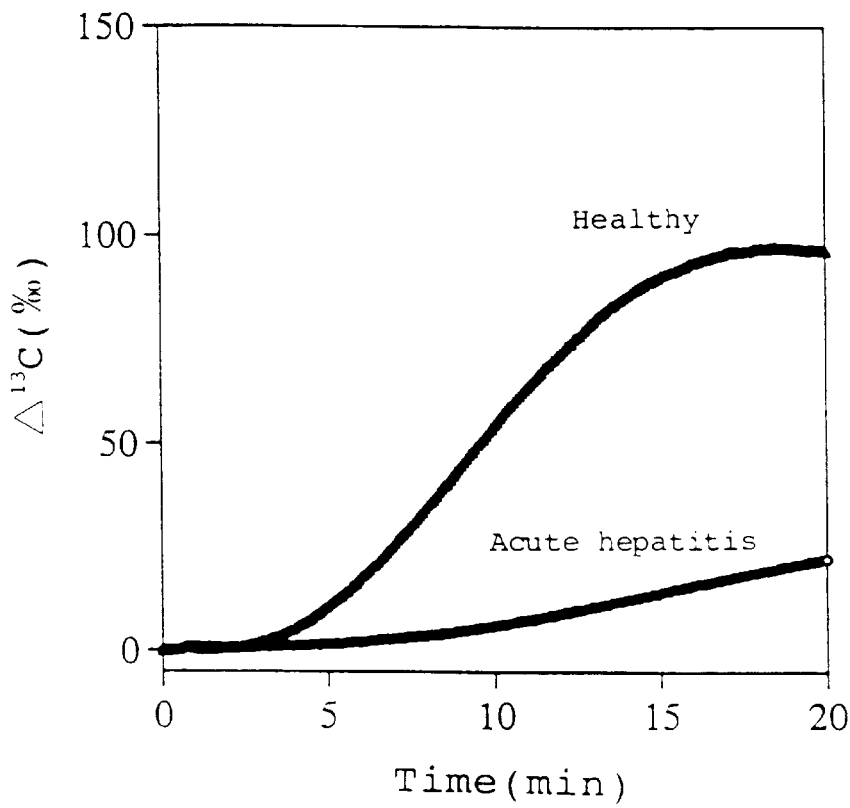

Increase of $^{13}CO_2$ in Exhalation
after Administration of $1\text{-}^{13}C$-Histidine $1\text{-}^{13}C$-histidine (30 mg/kg) was administered
intravenously to healthy rats (male SD; 8-week old; total
bilirubin value $\leq$ 0.5 mg/dl; n=4) and rats with acute
hepatitis (male SD; 8-week old; total bilirubin value > 4
mg/dl; n=4) at time 0. Then, degrees of increase of $^{13}C$
levels in exhaled $CO_2$ ($\Delta^{13}C$ (‰)) were measured. All the
rats were fasted overnight before the experiment.

FIG. 8

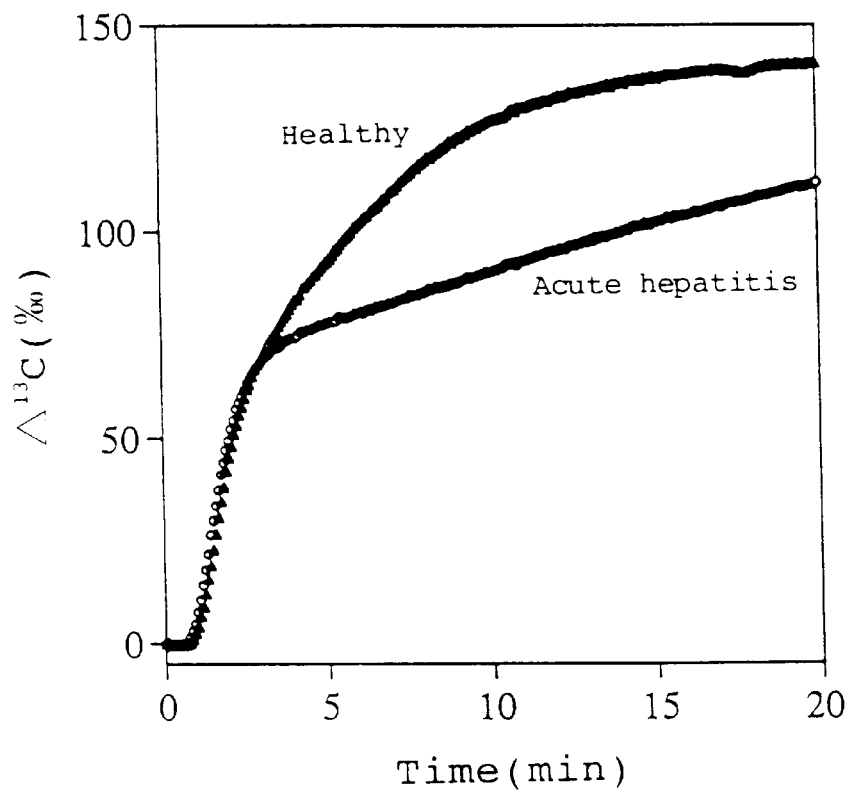

Increase of $^{13}CO_2$ in Exhalation
after Administration of 1,2-$^{13}$C-Ornithine 1,2-$^{13}$C-ornithine (20 mg/kg) was administered
intravenously to healthy rats (male SD; 8-week old; total
bilirubin value < 0.5 mg/dl; n=4) and rats with acute
hepatitis (male SD; 8-week old; total bilirubin value $\geq$ 2.2
mg/dl; n=4) at time 0. Then, degrees of increase of $^{13}$C
levels in exhaled $CO_2$ ($\Delta^{13}$C (‰)) were measured. All the
rats were fasted overnight before the experiment.

FIG. 9

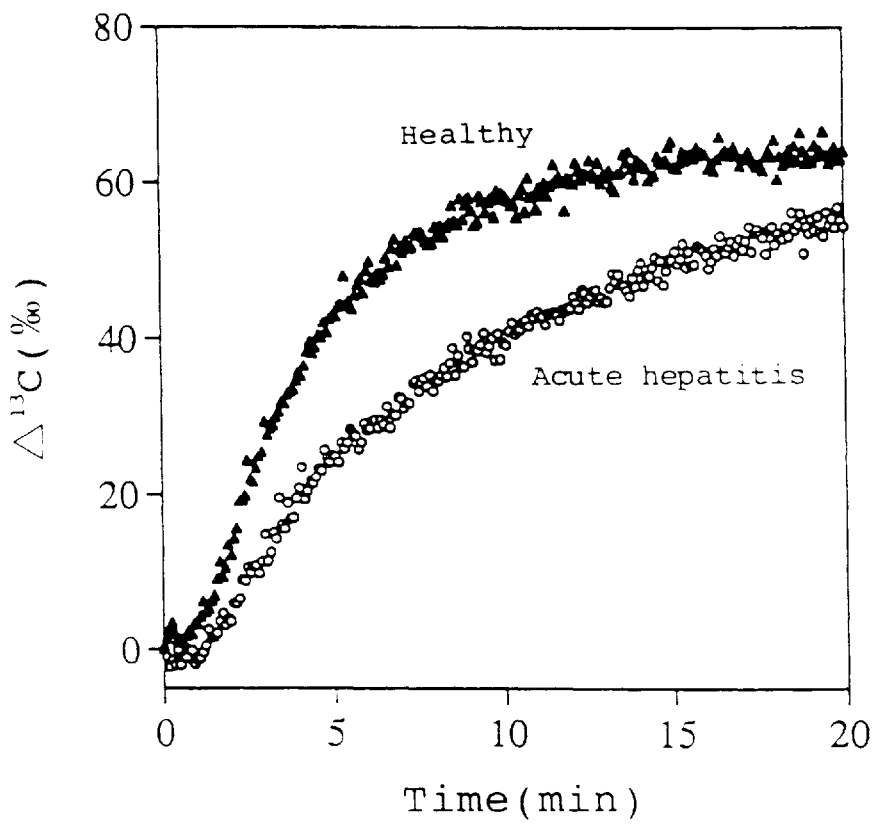

Increase of $^{13}CO_2$ in Exhalation
after Administration of 1-$^{13}$C-Valine

1-$^{13}$C-valine (20 mg/kg) was administered intravenously
to healthy rats (male SD; 8-week old; total bilirubin value
$\leq$ 0.6 mg/dl; n=4) and rats with acute hepatitis (male SD;
8-week old; total bilirubin value > 3.5 mg/dl; n=4) at time
0. Then, degrees of increase of $^{13}$C levels in exhaled $CO_2$
($\Delta^{13}$C (‰)) were measured. All the rats were fasted
overnight before the experiment.

FIG. 10

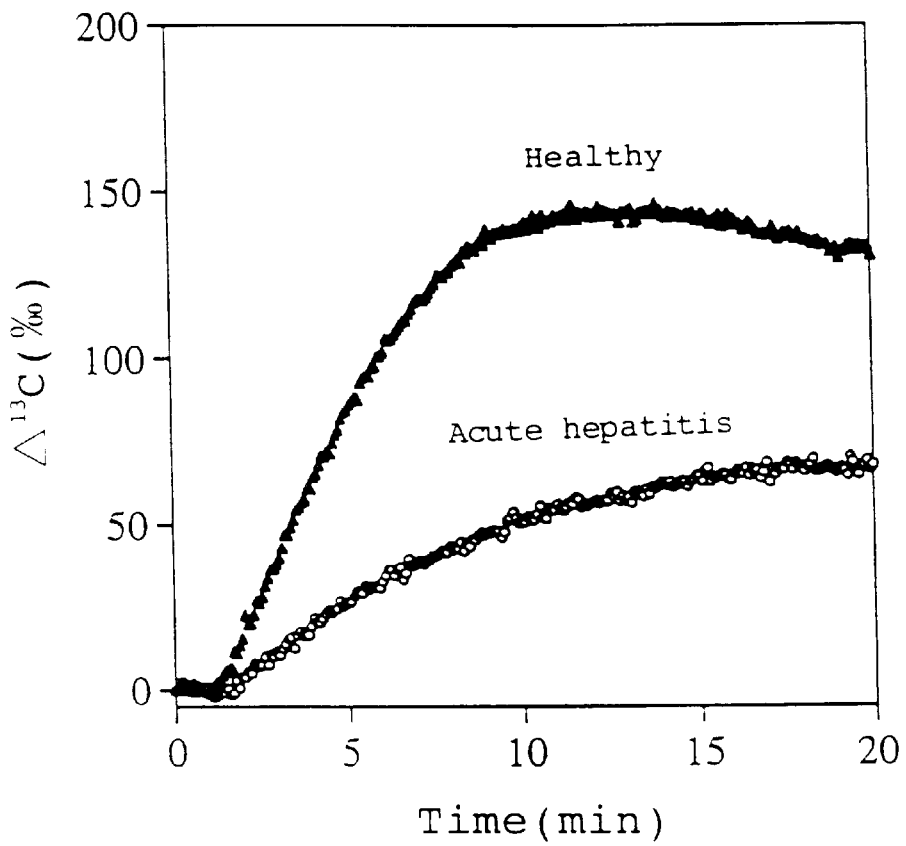

Increase of $^{13}CO_2$ in Exhalation
after Administration of 1-$^{13}$C-Lysine

1-$^{13}$C-lysine (50 mg/kg) was administered intravenously to healthy rats (male SD; 7-week old; total bilirubin value ≦ 0.7 mg/dl; n=4) and rats with acute hepatitis (male SD; 7-week old; total bilirubin value > 3.5 mg/dl; n=4) at time 0. Then, degrees of increase of $^{13}$C levels in exhaled $CO_2$ ($\Delta^{13}C$ (‰)) were measured. All the rats were fasted overnight before the experiment.

FIG. 11

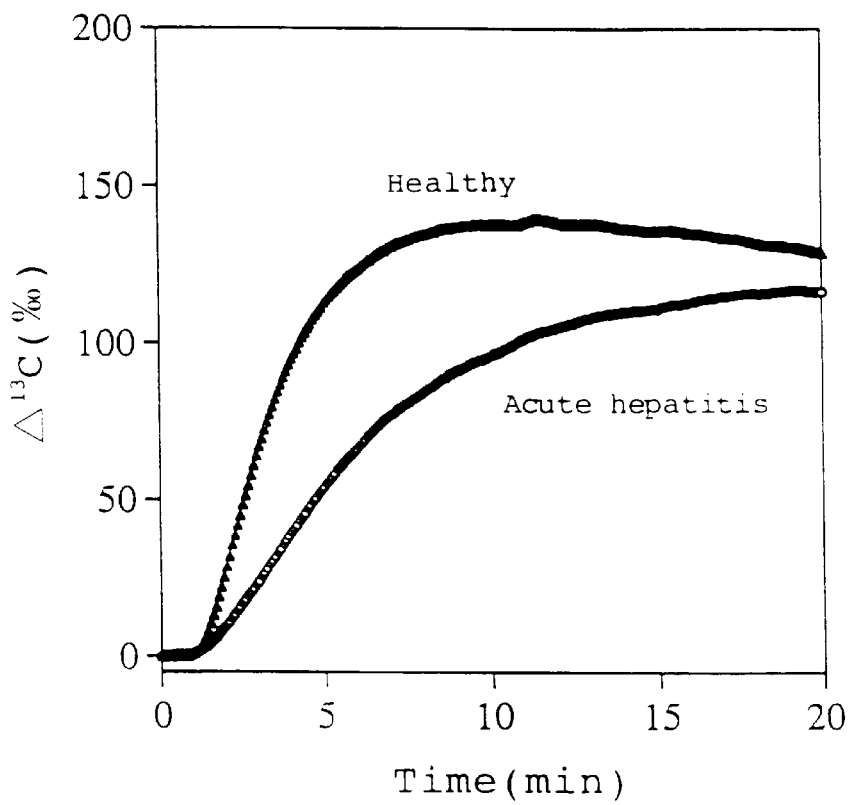

Increase of $^{13}CO_2$ in Exhalation
after Administration of 1-$^{13}$C-Serine

1-$^{13}$C-serine (50 mg/kg) was administered intravenously to healthy rats (male SD; 8-week old; total bilirubin value ≦ 0.6 mg/dl; n=4) and rats with acute hepatitis (male SD; 8-week old; total bilirubin value > 3 mg/dl; n=3) at time 0. Then, degrees of increase of $^{13}$C levels in exhaled $CO_2$ ($\Delta^{13}$C (‰)) were measured. All the rats were fasted overnight before the experiment.

FIG.12

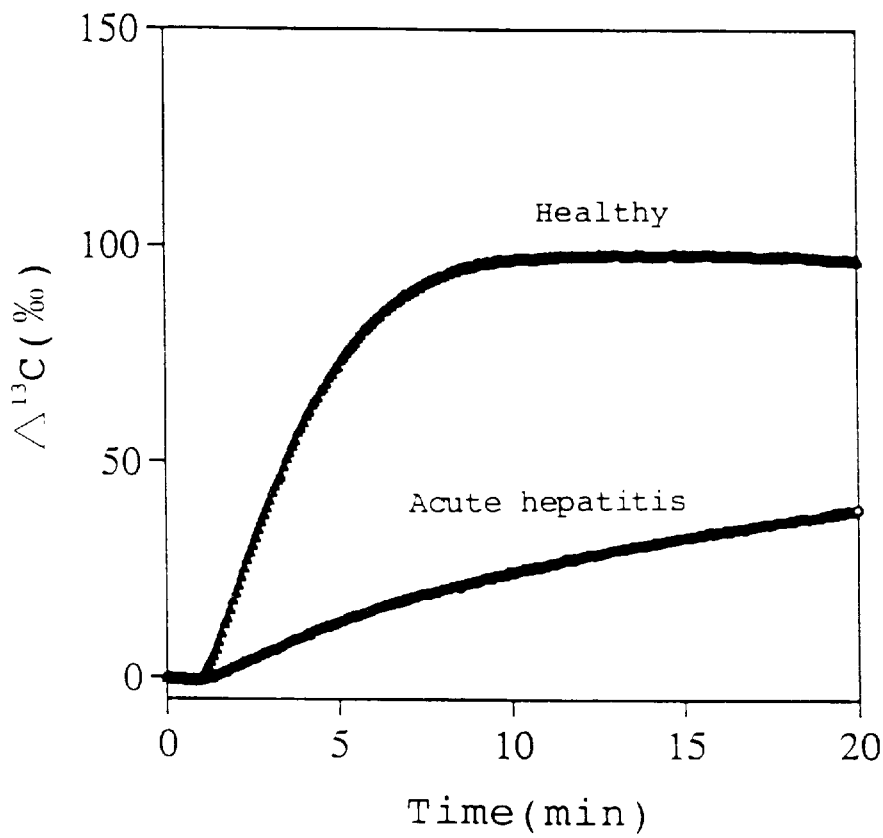

Increase of $^{13}CO_2$ in Exhalation
after Administration of 1-$^{13}$C-Threonine 1-$^{13}$C-threonine (50 mg/kg) was administered intravenously to healthy rats (male SD; 7-week old; total bilirubin value $\leq$ 0.6 mg/dl; n=4) and rats with acute hepatitis (male SD; 7-week old; total bilirubin value > 3 mg/dl; n=4) at time 0. Then, degrees of increase of $^{13}$C levels in exhaled $CO_2$ ($\Delta^{13}$C (‰)) were measured. All the rats were fasted overnight before the experiment.

FIG. 13

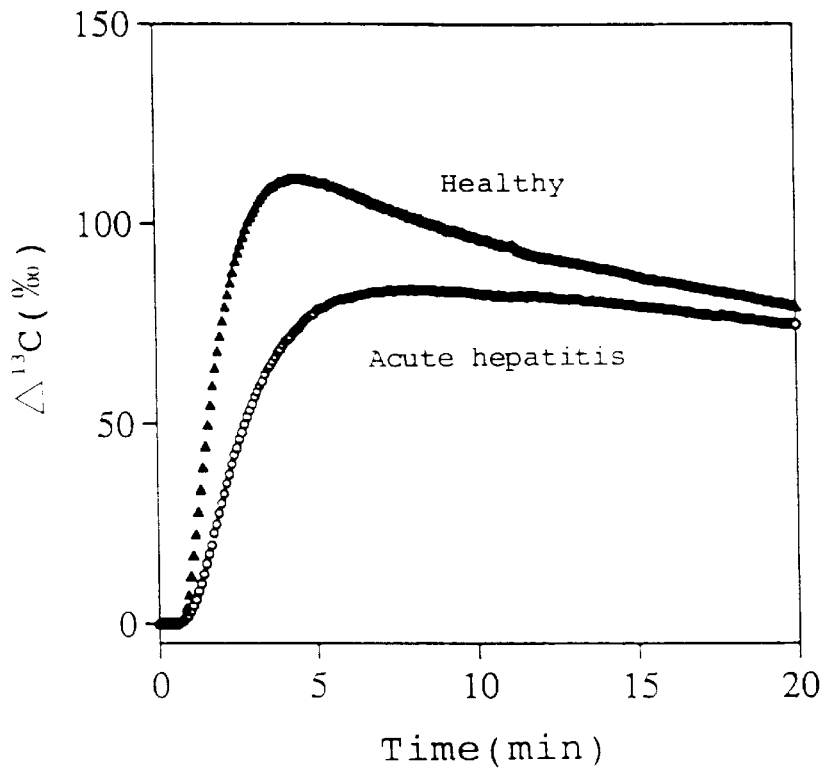

Increase of $^{13}CO_2$ in Exhalation
after Administration of 1-$^{13}$C-Cysteine 1-$^{13}$C-cysteine (20 mg/kg) was administered intravenously to healthy rats (male SD; 8-week old; total bilirubin value $\leq$ 0.5 mg/dl; n=4) and rats with acute hepatitis (male SD; 8-week old; total bilirubin value $\geq$ 2.1 mg/dl; n=2) at time 0. Then, degrees of increase of $^{13}$C levels in exhaled $CO_2$ ($\Delta^{13}C$ (‰)) were measured. All the rats were fasted overnight before the experiment.

FIG. 14

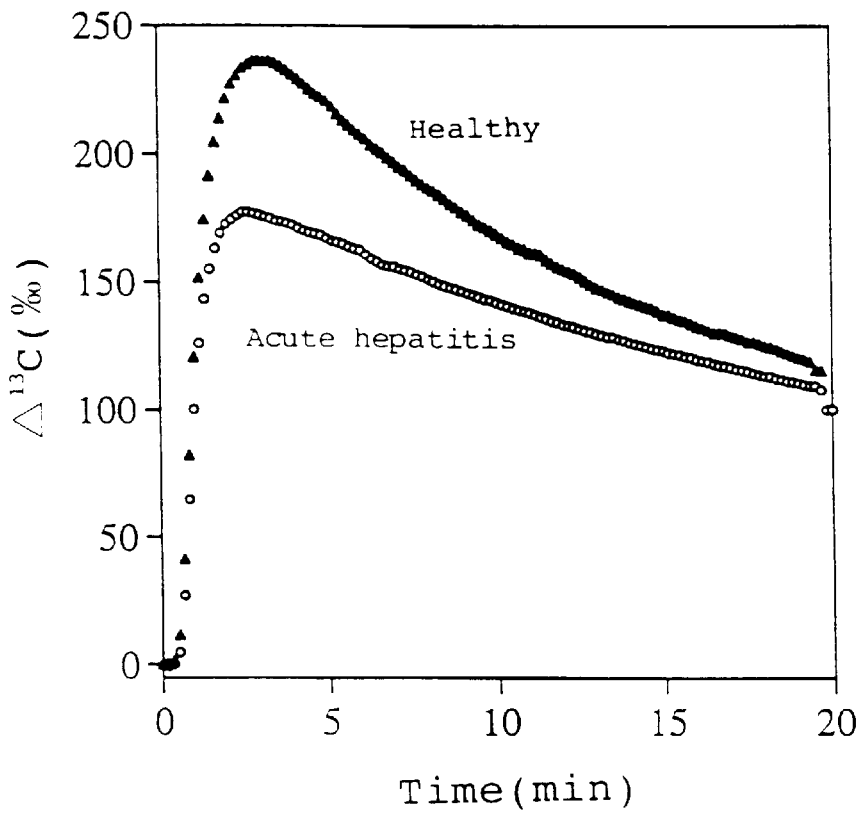

Increase of $^{13}CO_2$ in Exhalation
after Administration of $1-^{13}C$-Glutamic Acid $1-^{13}C$-glutamic acid (10 mg/kg) was administered intravenously to healthy rats (male SD; 8-week old; total bilirubin value $\leq$ 0.6 mg/dl; n=2) and rats with acute hepatitis (male SD; 8-week old; total bilirubin value > 4 mg/dl; n=4) at time 0. Then, degrees of increase of $^{13}C$ levels in exhaled $CO_2$ ($\Delta^{13}C$ (‰)) were measured. All the rats were fasted overnight before the experiment.

FIG.15

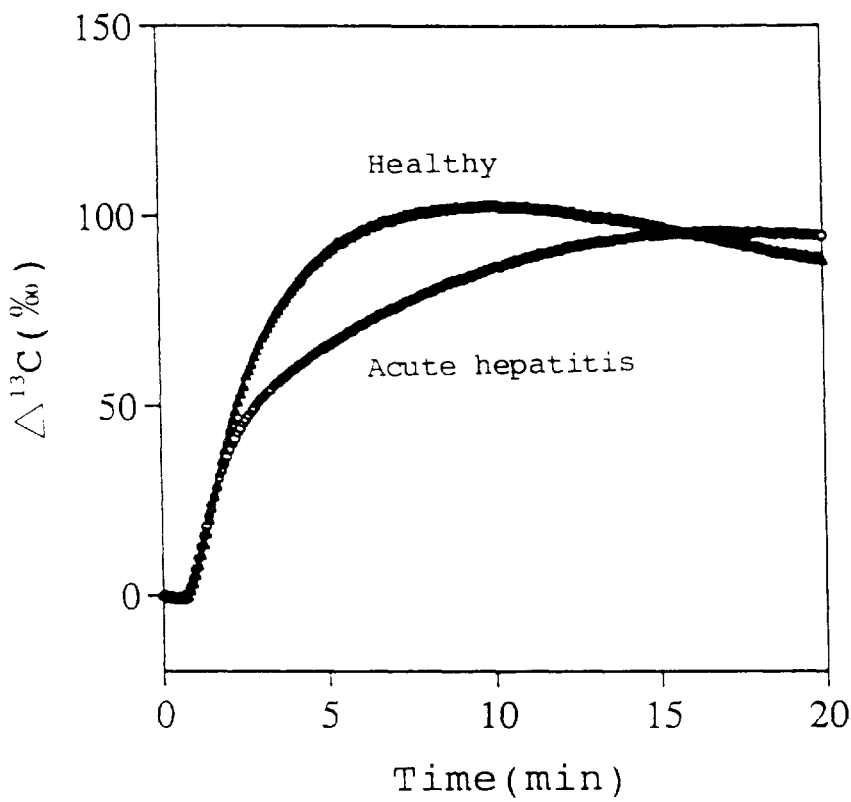

Increase of $^{13}CO_2$ in Exhalation
after Administration of $1\text{-}^{13}C\text{-Proline}$ $1\text{-}^{13}C$-proline (20 mg/kg) was administered intravenously to healthy rats (male SD; 8-week old; total bilirubin value < 0.5 mg/dl; n=4) and rats with acute hepatitis (male SD; 8-week old; total bilirubin value $\geq$ 1.5 mg/dl; n=4) at time 0. Then, degrees of increase of $^{13}C$ levels in exhaled $CO_2$ ($\Delta^{13}C$ (‰)) were measured. All the rats were fasted overnight before the experiment.

FIG. 16

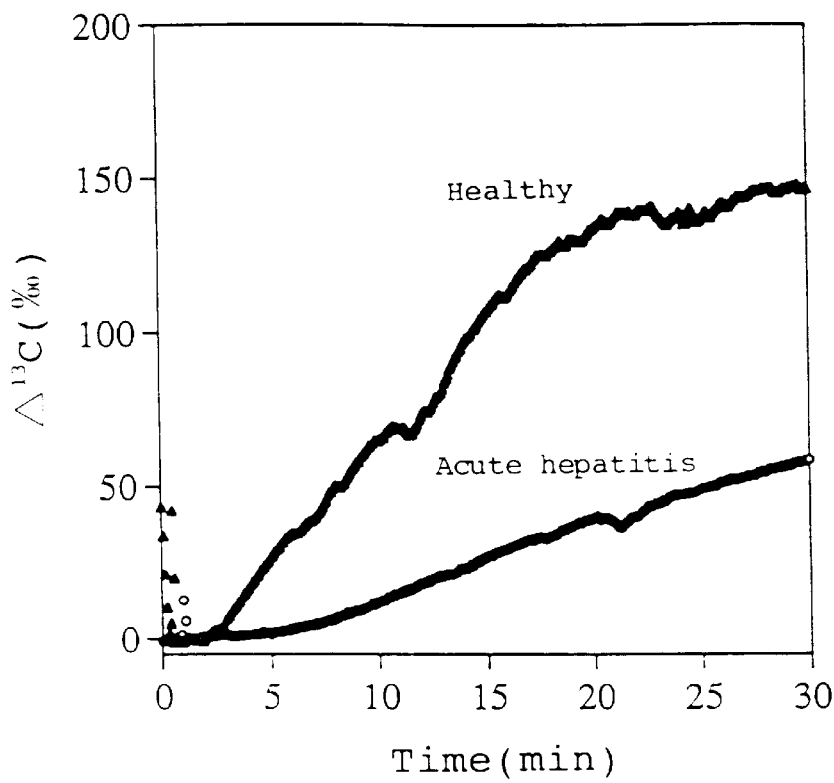

Increase of $^{13}CO_2$ in Exhalation
after Administration of $1,1$-$^{13}C$-Cystine $1,1$-$^{13}C$-cystine (45 mg/kg) was administered orally to
healthy rats (male SD; 9-week old; total bilirubin value $\leq$
0.6 mg/dl; n=4) and rats with acute hepatitis (male SD; 9-
week old; total bilirubin value $\geq$ 4.5 mg/dl; n=4) at time 0.
Then, degrees of increase of $^{13}C$ levels in exhaled $CO_2$ ($\Delta^{13}C$
(‰)) were measured. All the rats were fasted overnight
before the experiment.

FIG. 17

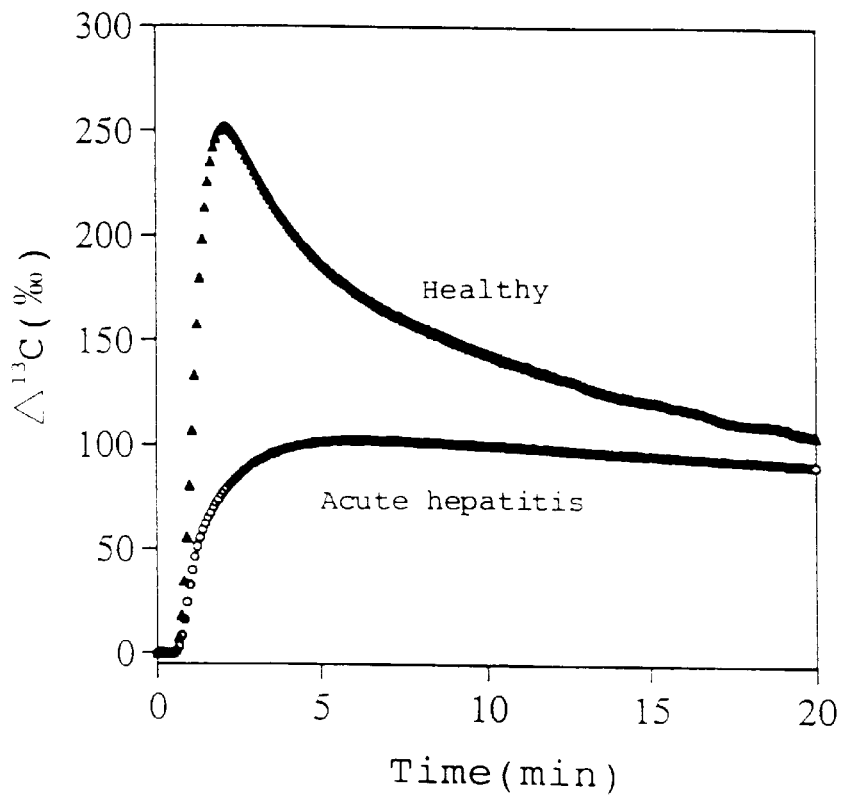

Increase of $^{13}CO_2$ in Exhalation
after Administration of $1-^{13}C$-Lactic Acid $1-^{13}C$-sodium lactate (10 mg/kg) was administered intravenously to healthy rats (male SD; 8-week old; total bilirubin value ≦ 0.6 mg/dl; n=4) and rats with acute hepatitis (male SD; 8-week old; total bilirubin value > 3.5 mg/dl; n=4) at time 0. Then, degrees of increase of $^{13}C$ levels in exhaled $CO_2$ ($\Delta^{13}C$ (‰)) were measured. All the rats were fasted overnight before the experiment.

FIG. 18

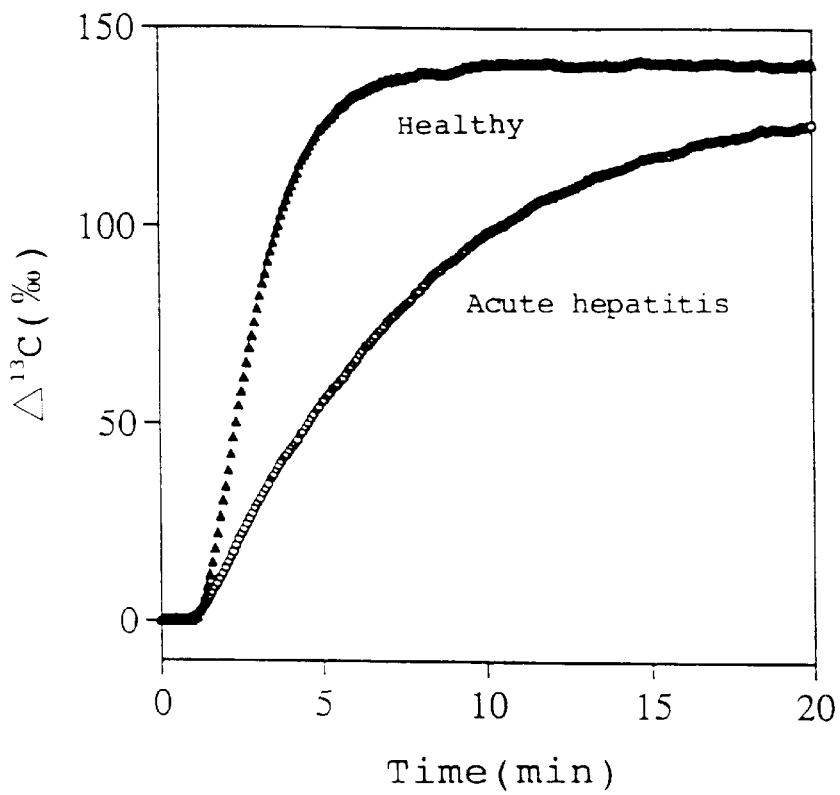

Increase of $^{13}CO_2$ in Exhalation
after Administration of $3-^{13}C$-Lactic Acid $3-^{13}C$-sodium lactate (50 mg/kg) was administered intravenously to healthy rats (male SD; 10-week old; total bilirubin value = 0.3 mg/dl; n=3) and rats with acute hepatitis (male SD; 10-week old; total bilirubin value $\geq$ 2.5 mg/dl; n=6) at time 0. Then, degrees of increase of $^{13}C$ levels in exhaled $CO_2$ ($\Delta^{13}C$ (‰)) were measured. All the rats were fasted overnight before the experiment.

FIG.19

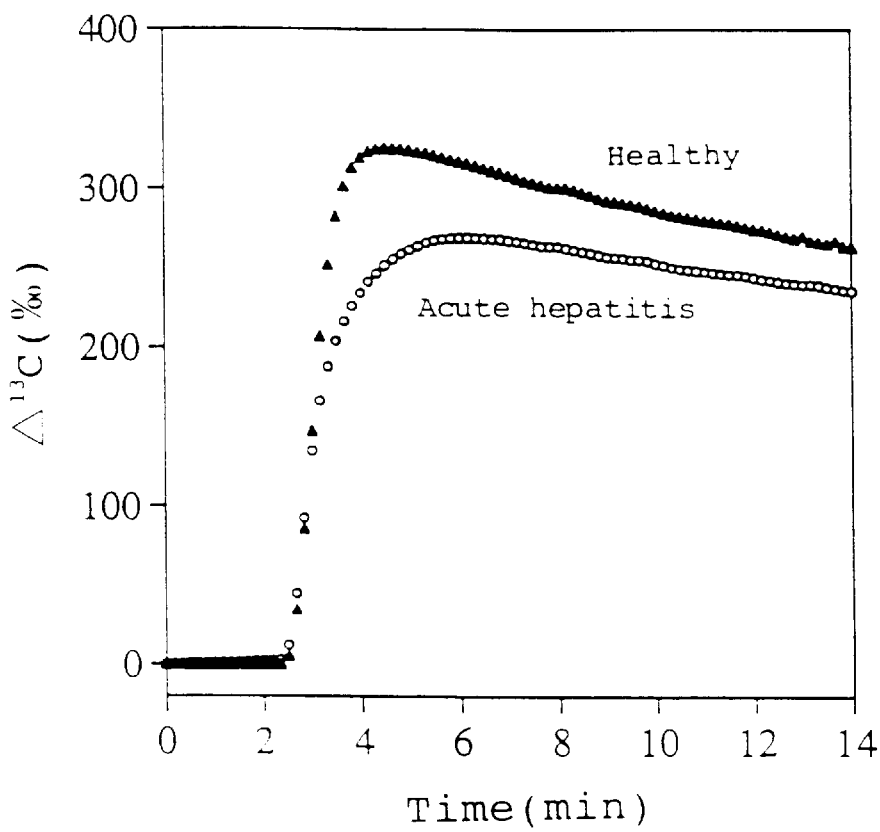

Increase of $^{13}CO_2$ in Exhalation
after Administration of 1-$^{13}$C-Pyruvic Acid 1-$^{13}$C-sodium pyruvate (20 mg/kg) was administered intravenously to healthy rats (male SD; 8-week old; total bilirubin value ≦ 0.5 mg/dl; n=4) and rats with acute hepatitis (male SD; 8-week old; total bilirubin value > 3 mg/dl; n=4) at time 0. Then, degrees of increase of $^{13}$C levels in exhaled $CO_2$ ($\Delta^{13}C$ (‰)) were measured. All the rats were fasted overnight before the experiment.

FIG. 20

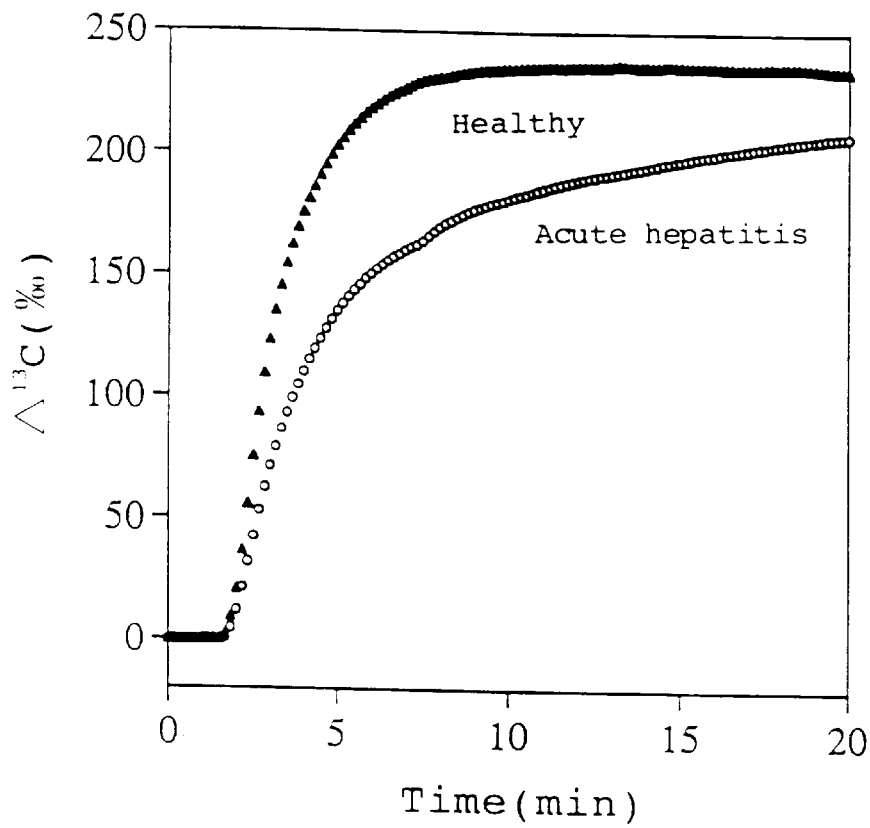

Increase of $^{13}CO_2$ in Exhalation
after Administration of 3-$^{13}$C-Pyruvic Acid 3-$^{13}$C-sodium pyruvate (20 mg/kg) was administered intravenously to healthy rats (male SD; 8-week old; total bilirubin value < 0.5 mg/dl; n=4) and rats with acute hepatitis (male SD; 8-week old; total bilirubin value > 3.5 mg/dl; n=4) at time 0. Then, degrees of increase of $^{13}$C levels in exhaled $CO_2$ ($\triangle^{13}C$ (‰)) were measured. All the rats were fasted overnight before the experiment.

FIG.21

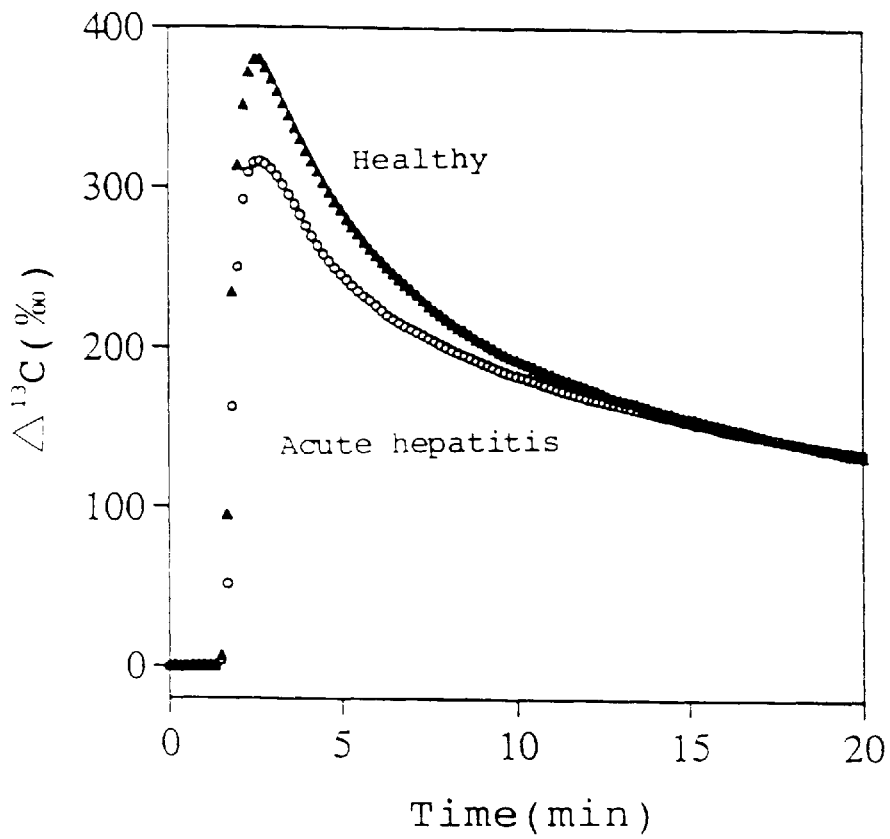

Increase of $^{13}CO_2$ in Exhalation
after Administration of $1,4-^{13}C$-Succinic Acid $1,4-^{13}C$-succinic acid (4 mg/kg) was administered intravenously to healthy rats (male SD; 10-week old; total bilirubin value $\leq$ 0.5 mg/dl; n=3) and rats with acute hepatitis (male SD; 10-week old; total bilirubin value > 4 mg/dl; n=4) at time 0. Then, degrees of increase of $^{13}C$ levels in exhaled $CO_2$ ($\Delta^{13}C$ (‰)) were measured. All the rats were fasted overnight before the experiment.

FIG.22

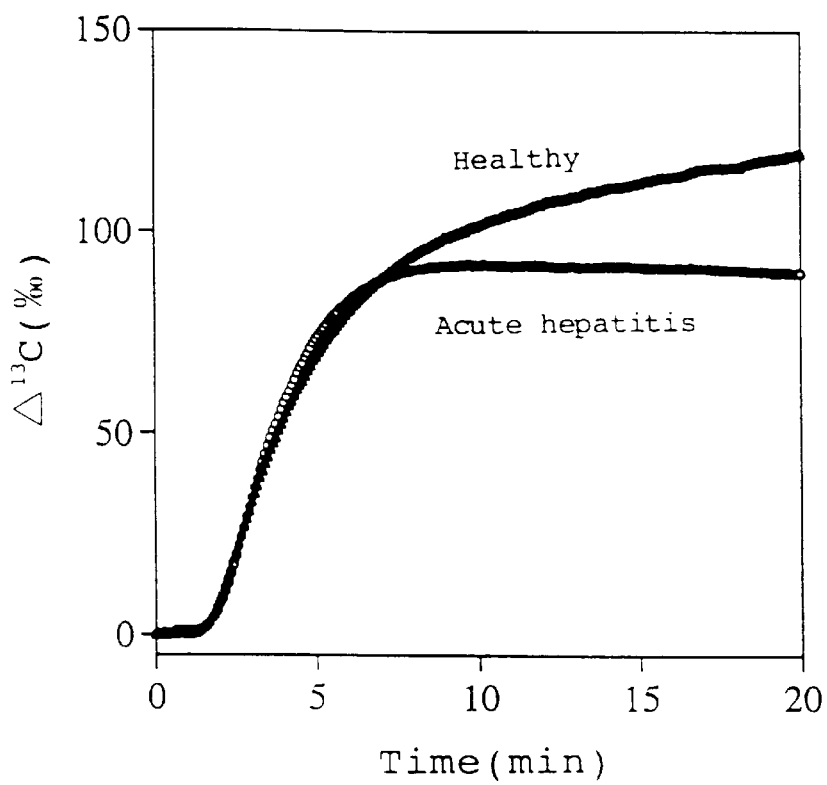

Increase of $^{13}CO_2$ in Exhalation
after Administration of $1-^{13}C$-Oleic Acid $1-^{13}C$-oleic acid (70 mg/kg) was administered intravenously to healthy rats (male SD; 8-week old; total bilirubin value $\leq$ 0.7 mg/dl; n=4) and rats with acute hepatitis (male SD; 8-week old; total bilirubin value $\geq$ 2.4 mg/dl; n=4) at time 0. Then, degrees of increase of $^{13}C$ levels in exhaled $CO_2$ ($\Delta^{13}C$ (‰)) were measured. All the rats were fasted overnight before the experiment.

FIG.23

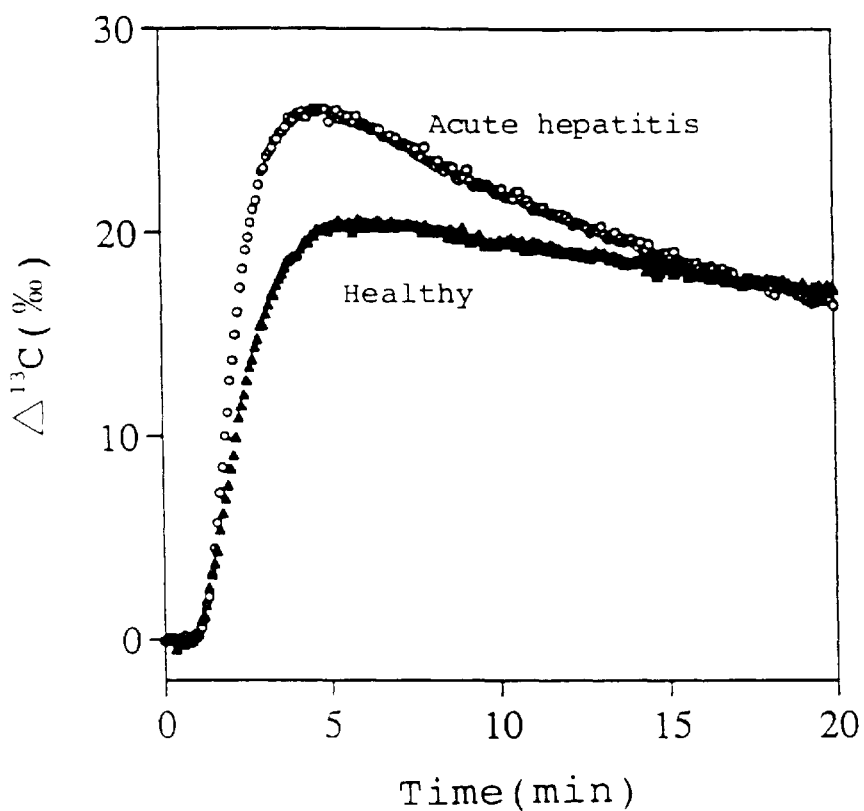

Increase of $^{13}CO_2$ in Exhalation
after Administration of $1-^{13}C$-Octanoic Acid $1-^{13}C$-octanoic acid (30 mg/kg) was administered
intravenously to healthy rats (male SD; 8-week old; total
bilirubin value $\leq$ 0.7 mg/dl; n=4) and rats with acute
hepatitis (male SD; 8-week old; total bilirubin value > 2.5
mg/dl; n=4) at time 0. Then, degrees of increase of $^{13}C$
levels in exhaled $CO_2$ ($\Delta^{13}C$ (‰)) were measured. All the
rats were fasted overnight before the experiment.

FIG. 24

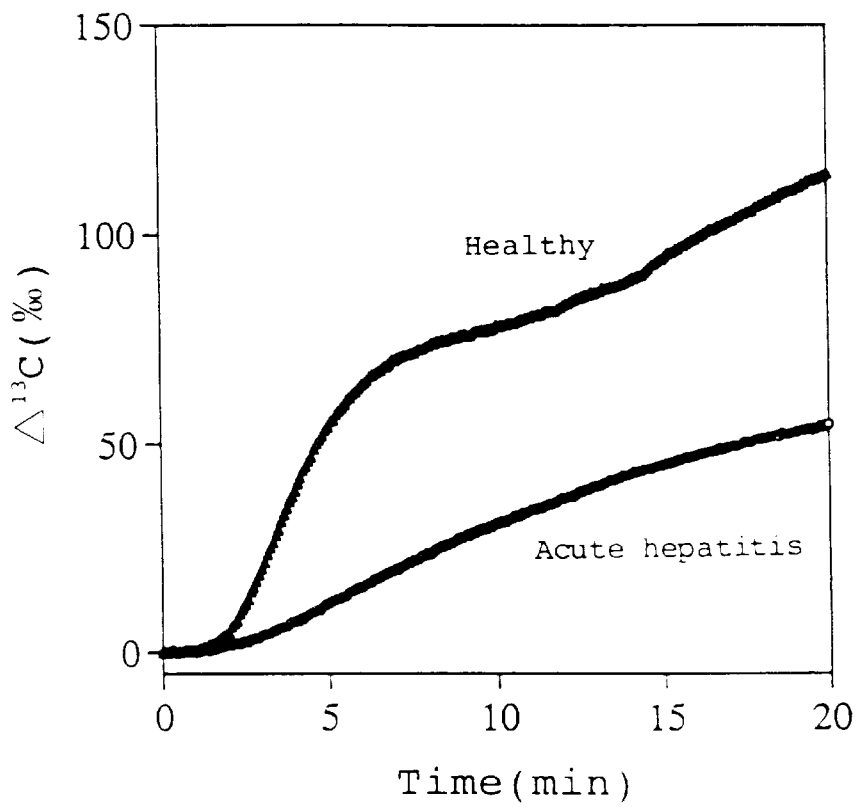

Increase of $^{13}CO_2$ in Exhalation
after Administration of 1,1,1-$^{13}$C-Trioctanoin 1,1,1-$^{13}$C-trioctanoin (30 mg/kg) was administered intravenously to healthy rats (male SD; 8-week old; total bilirubin value $\leqq$ 0.6 mg/dl; n=4) and rats with acute hepatitis (male SD; 8-week old; total bilirubin value $\geqq$ 3.5 mg/dl; n=4) at time 0. Then, degrees of increase of $^{13}$C levels in exhaled $CO_2$ ($\Delta^{13}C$ (‰)) were measured. All the rats were fasted overnight before the experiment.

FIG. 25

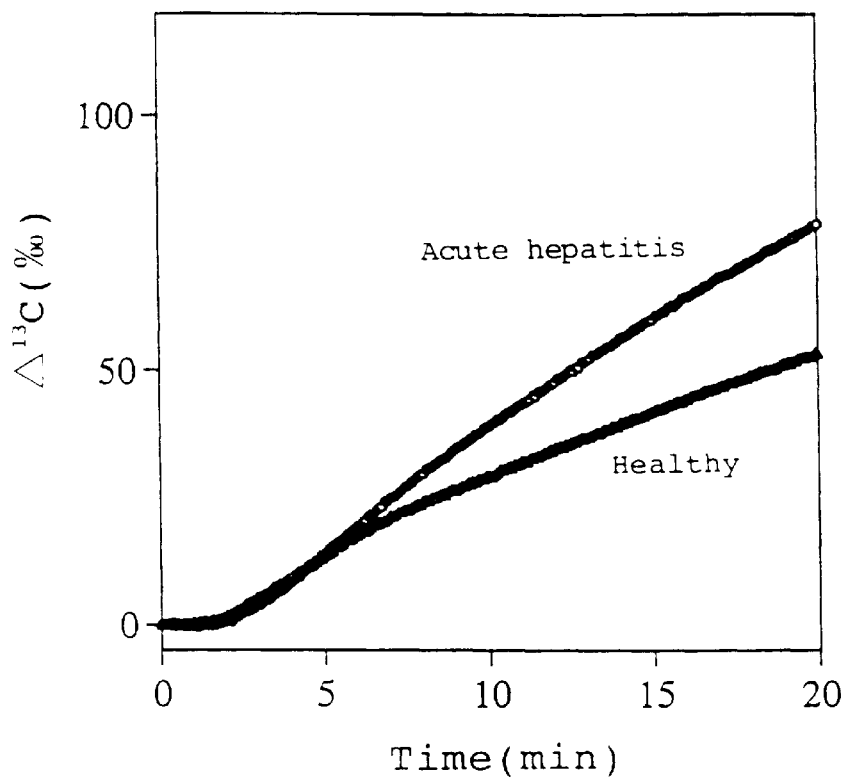

Increase of $^{13}CO_2$ in Exhalation
after Administration of $2-^{13}C$-Glycerol $2-^{13}C$-glycerol (50 mg/kg) was administered intravenously
to healthy rats (male SD; 8-week old; total bilirubin value
$\leq$ 0.5 mg/dl; n=4) and rats with acute hepatitis (male SD;
8-week old; total bilirubin value > 3.5 mg/dl; n=4) at time
0. Then, degrees of increase of $^{13}C$ levels in exhaled $CO_2$
($\Delta^{13}C$ (‰)) were measured. All the rats were fasted
overnight before the experiment.

DIAGNOSTIC AGENT FOR LIVER FUNCTION

BACKGROUND OF THE INVENTION

The present invention relates to a diagnostic agent for liver function. More specifically, the invention relates to a diagnostic agent for liver function, comprising a compound labelled with $^{13}C$ at least at one specific position.

DESCRIPTION OF THE PRIOR ART

Test methods generally used in the screening of liver function disorder are blood biochemical tests to quantitatively determine enzymes such as transaminases (GPT and GOT), alkaline phosphatase (ALP) and lactate dehydrogenase (LDH) in blood. These enzymes leak out from the liver tissue of a patient into the blood when he/she has a liver function disorder. Among all, GPT and GOT are enzymes mainly present in the liver. While their blood levels are low under normal conditions, the levels increase remarkably at the time of liver function disorders. Thus, GPT and GOT are excellent indicators which detect liver function disorders sensitively. However, in the case of patients suffering from chronic hepatitis or cirrhosis whose liver function is remarkably lowered, enzyme leakage from the liver decreases since the amounts of enzymes present in the liver tissue decrease. Thus, enzyme leakage may not exhibit high values even when the degree of disorder is high (Diagnosis and Treatment Today, CD-ROM Vol. 6, Igaku-Shoin Ltd.). Besides, since it will take some time for the leaked out enzymes to disappear from the blood, high values may be obtained from a subject who has been already recovered from a liver function disorder at the time of the test. Therefore, quantitative determination of these enzymes is insufficient as a test method to evaluate the degree of a liver function disorder.

In particular, at the time of a surgical operation of a liver, it is very important to evaluate the degree of a hepatic disorder and the liver function of a patient (Practice of Diagnosis & Treatment in Digestive Apparatuses 1: Diagnostic Approach to Hepatic Disorders, Teruyuki Ohkubo (Ed.), Bunko-Do Co.). At present, determination of serum bilirubin levels and ICG tolerance test are mainly conducted for the evaluation of the degree of a hepatic disorder and the liver function. However, these tests have problems, respectively (Practice of Diagnosis & Treatment in Digestive Apparatuses 1: Diagnostic Approach to Hepatic Disorders, Teruyuki Ohkubo (Ed.), Bunko-Do Co.). For example, increase in serum bilirubin level not necessarily indicates the lowering of liver function. Besides, it is difficult to follow those processes in which liver function changes drastically for a short period of time after a hepatic operation. In ICG tolerance test, reliable results cannot be obtained when bilirubin levels are high, because ICG competes with bilirubin when it is taken into liver cells. Under such circumstances, a means is desired by which the degree of a hepatic disorder and the liver function of a subject at the time of a test can be evaluated safely and simply regardless of the conditions of the subject.

OBJECTS AND SUMMARY OF THE INVENTION

It is an object of the present invention to provide a diagnostic agent for liver function which can evaluate the liver function of a subject safely and simply regardless of the conditions of the subject.

As a result of intensive and extensive researches, the present inventors have found that it is possible to diagnose the liver function of a subject correctly by administering to the subject a compound labelled with $^{13}C$ at least at one specific position and measuring the degrees of increase of $^{13}C$ levels in the exhaled $CO_2$. Thus, the present invention has been achieved.

The present invention relates to a diagnostic agent for liver function, comprising a compound labelled with $^{13}C$ at least at one specific position selected from the group consisting of the following (a) to (f):

(a) galactose, glucose or xylose labelled with $^{13}C$ at least at one specific position or a starch composed of glucose units labelled with $^{13}C$ at least at one specific position;

(b) a polar amino acid, heterocyclic amino acid, isoleucine or valine labelled with $^{13}C$ at least at one specific position;

(c) a carboxylic acid constituting the glycolytic pathway or the citric acid cycle, labelled with $^{13}C$ at least at one specific position;

(d) a fatty acid labelled with $^{13}C$ at least at one specific position;

(e) a glyceride labelled with $^{13}C$ at least at one specific position; and (f) glycerol labelled with $^{13}C$ at least at one specific position.

BRIEF DESCRIPTION OF THE DRAWINGS

FIG. 1 is a schematic illustration of a method for recovering exhalation from a rat.

FIG. 2 shows the increase of $^{13}CO_2$ in exhalation after administration of 1-$^{13}C$-galactose.

FIG. 3 shows the increase of $^{13}CO_2$ in exhalation after administration of 1-$^{13}C$-glucose.

FIG. 4 shows the increase of $^{13}CO_2$ in exhalation after administration of 3-$^{13}C$-glucose.

FIG. 5 shows the increase of $^{13}CO_2$ in exhalation after administration of U-$^{13}C$-starch.

FIG. 6 shows the increase of $^{13}CO_2$ in exhalation after administration of 1-$^{13}C$-arginine.

FIG. 7 shows the increase of $^{13}CO_2$ in exhalation after administration of 1-$^{13}C$-histidine.

FIG. 8 shows the increase of $^{13}CO_2$ in exhalation after administration of 1,2-$^{13}C$-ornithine.

FIG. 9 shows the increase of $^{13}CO_2$ in exhalation after administration of 1-$^{13}C$-valine.

FIG. 10 shows the increase of $^{13}CO_2$ in exhalation after administration of 1-$^{13}C$-lysine.

FIG. 11 shows the increase of $^{13}CO_2$ in exhalation after administration of 1-$^{13}C$-serine.

FIG. 12 shows the increase of $^{13}CO_2$ in exhalation after administration of 1-$^{13}C$-threonine.

FIG. 13 shows the increase of $^{13}CO_2$ in exhalation after administration of 1-$^{13}C$-cysteine.

FIG. 14 shows the increase of $^{13}CO_2$ in exhalation after administration of 1-$^{13}C$-glutamic acid.

FIG. 15 shows the increase of $^{13}CO_2$ in exhalation after administration of 1-$^{13}C$-proline.

FIG. 16 shows the increase of $^{13}CO_2$ in exhalation after administration of 1,1-$^{13}C$-cystine.

FIG. 17 shows the increase of $^{13}CO_2$ in exhalation after administration of 1-$^{13}C$-lactic acid.

FIG. 18 shows the increase of $^{13}CO_2$ in exhalation after administration of 3-$^{13}C$-lactic acid.

FIG. 19 shows the increase of $^{13}CO_2$ in exhalation after administration of 1-$^{13}C$-pyruvic acid.

FIG. 20 shows the increase of $^{13}CO_2$ in exhalation after administration of 3-$^{13}C$-pyruvic acid.

FIG. 21 shows the increase of $^{13}CO_2$ in exhalation after administration of 1,4-$^{13}$C-succinic acid.

FIG. 22 shows the increase of $^{13}CO_2$ in exhalation after administration of 1-$^{13}$C-oleic acid.

FIG. 23 shows the increase of $^{13}CO_2$ in exhalation after administration of 1-$^{13}$C-octanoic acid.

FIG. 24 shows the increase of $^{13}CO_2$ in exhalation after administration of 1,1,1-$^{13}$C-trioctanoin.

FIG. 25 shows the increase of $^{13}CO_2$ in exhalation after administration of 2-$^{13}$C-glycerol.

DETAILED DESCRIPTION OF THE INVENTION

Hereinbelow, the present invention will be described in detail.

In the diagnostic agent of the invention for liver function, galactose, glucose or xylose labelled with $^{13}$C at least at one specific position or a starch composed of glucose units labelled with $^{13}$C at least at one specific position may be used. The position of the labelling is not particularly limited.

Alternatively, a polar amino acid, heterocyclic amino acid, isoleucine or valine labelled with $^{13}$C at least at one specific position may be used in the diagnostic agent of the intention for liver function. The position of the labelling is not particularly limited.

As the polar amino acid, preferable examples includes, but are not limited to, arginine, asparagine, aspartic acid, glutamine, glutamic acid, cysteine, cystine, glycine, lysine, serine, threonine, tyrosine and ornithine. As the heterocyclic amino acid, preferable examples includes, but are not limited to, tryptophan, proline and histidine.

Alternatively, a carboxylic acid constituting the glycolytic pathway or the citric acid cycle, labelled with $^{13}$C at least at one specific position may be used in the diagnostic agent of the invention for liver function. The position of the labelling is not particularly limited.

As the carboxylic acid constituting the glycolytic pathway or the citric acid cycle, preferable examples include, but are not limited to, pyruvic acid, lactic acid, succinic acid and citric acid.

Alternatively, a fatty acid labelled with $^{13}$C at least at one specific position may be used in the diagnostic agent of the invention for liver function. The position of the labelling is not particularly limited.

As the fatty acid, preferable examples include, but are not limited to, octanoic acid, palmitic acid, oleic acid, linolic acid and linolenic acid.

Alternatively, a glyceride labelled with $^{13}$C at least at one specific position may be used in the diagnostic agent of the invention for liver function. The position of the labelling is not particularly limited.

As the glyceride, preferable examples include, but are not limited to, trioctanoin, tripalmitin and triolein.

Alternatively, glycerol labelled with $^{13}$C at least at one specific position may be used in the diagnostic agent of the invention for liver function. The position of the labelling is not particularly limited.

The above-mentioned compounds used in the present invention are contained in foods. Further, unlike radioisotopes, $^{13}$C is a stable isotope. Thus, there is no danger of exposure to radiation. Accordingly, the diagnostic agent of the invention has no problem in its safety.

The test using the diagnostic agent of the invention is a breath test in which the agent is administered to a subject once or a plurality of times and then the increase of $^{13}$C levels in the exhaled $CO_2$ is measured. Specifically, $^{13}$C levels in the exhaled $CO_2$ after administration of the agent are measured, followed by evaluation of the subject's liver function from data on the degree of increase of $^{13}$C levels in the exhaled $CO_2$ ($\Delta^{13}C$ (‰)) at predetermined intervals (e.g., 5 min, 10 min, 15 min) after the administration, total amount of $^{13}CO_2$ exhalation for a predetermined time after administration of the reagent or on the time course (slope at the start, change in the slope, peak time, etc.) of the degree of increase of $^{13}$C levels in the exhaled $CO_2$ ($\Delta^{13}C$ (‰)) for a predetermined time period after the administration. The results of such a breath test are useful by themselves. However, it is more preferable to use these results in combination with bilirubin values or the like for the judgement of liver function.

$^{13}$C levels in exhaled $CO_2$ can be determined using gas chromatography mass spectrometry (GC-MS), infrared spectrophotometry, mass spectrometry, photoelectric acoustic spectrophotometry and NMR (nuclear magnetic resonance).

The diagnostic agent of the invention for liver function can be formulated into pharmaceutical preparations such as parenteral agents (tablets, capsules, powder, granules, liquid, etc.), injections and the like, depending on the administration route, by using the above-described compound labelled with $^{13}$C at least at one specific position alone or mixing it with fillers or carriers. The fillers or carriers may be any of those conventionally used in this field as long as they are pharmaceutically acceptable. The type and composition of such pharmaceutical preparations are altered appropriately according to the route and method of administration. For example, water is used as a liquid carrier. As solid carriers, cellulose derivatives such as hydroxypropyl cellulose and organic acid salts such as magnesium stearate are used. Water, physiological saline and various buffer solutions are generally desirable in the preparation of injections. Such preparations may be lyophilized for use as oral agents, or the lyophilized preparations may be dissolved in suitable injection solvents e.g. liquids for intravenous administration (such as sterilized water, physiological saline, electrolyte, etc.) just before use.

The content of the labelled compound in the pharmaceutical preparation varies according to the type of the preparation, and is usually in the range of 1 to 100% by weight, preferably 50 to 100% by weight. In the case of injections, for example, the labelled compound is added usually in an amount of 1 to 40% by weight. In the case of capsules, tablets, granules and powder, the content of the labelled compound is in the range from about 10 to 100% by weight, preferably 50 to 100% by weight, with the remainder being carriers.

The diagnostic agent of the invention for liver function should be administered at such a dosage that enables the confirmation of an increase of $^{13}CO_2$ in an exhalation after administration of the diagnostic agent. Depending on the age and weight of the patient and the object of the test, the dosage for each administration ranges from 1 to 1000 mg/kg body weight in the case of an adult.

The diagnostic agent of the invention for liver function can be used for diagnosis of hepatic diseases or disorders such as cirrhosis, chronic hepatitis, acute hepatitis, hepatic cancer, etc. and for evaluation of liver function before and after a surgical operation of a liver.

EFFECT OF THE INVENTION

According to the present invention, there is provided a diagnostic agent for liver function which imposes less physical burden on a subject, can give accurate test results immediately, and can be used safely without side effects. The diagnostic agent of the invention is useful for evaluating the liver function at the test time.

PREFERRED EMBODIMENTS OF THE INVENTION

Hereinbelow, the present invention will be described more specifically below with reference to the following Examples. However, the scope of the present invention is not limited to these Examples.

The $^{13}$C purity at the position of labelling in each of the compounds used in the present invention is 99% or more. Unless otherwise indicated, all the reagents used were guaranteed reagents.

EXAMPLE 1

Method of Breath Test
(1) Preparation of Rats with Acute Hepatitis

As test animals, male Sprague-Dawley (SD) rats were purchased from Nippon Charles River K.K. They were bred at 23±2° C. under 55±10% humidity before use. These rats (7–10 week-old) were anesthetized by intraperitoneal administration of Nembutal (50 mg/kg) and then intraperitoneally administered galactosamine hydrochloride (200 mg/ml physiological saline) at a dose of 0.6–1.2 g/kg [Koff, S. et al., Proc. Soc. Exptl. Med. 137:696 (1971); Keppler, D. et al., Exp. Mol. Pathology, 9:279 (1968); Creation of Model Animals (by Disease) and Experimental Methods for Development of New Drugs, supervised by Masaharu Uchitaka, p. 126 (1993)]. Two days thereafter, blood was collected from the tail vein, and serum was separated from the blood. Glutamic pyruvic transaminase activity (GPT) and the total amount of bilirubin in the serum were measured using Fuji Drychem FDC5500.

(2) $^{13}$C Breath Test

A breath test was carried out as described below on the rats with acute hepatitis prepared in (1) above and healthy rats. The method described in (2)-2 below was used for labelled starch and labelled cystine, and the method described in (2)-1 was used for the other compounds.

(2)-1 Intravenous Administration

Rats fasted overnight were anesthetized by intraperitoneal administration of Nembutal (50 mg/kg) and fixed on an operation table. The head was covered with a cap for sucking the exhalation. A specific amount of the labelled compound was administered from the femoral vein. The exhalation was sucked with a stroke pump (variable stroke pump VS-500; Shibata Scientific Technology) at a rate of 100 ml/min and introduced directly into a flow cell in $^{13}$CO$_2$ Analyzer EX-130S (Japan Spectroscopic Co., Ltd.). A Perma Pure Drier (MD-050-12P; Perma Pure Inc.) was located between the cap and the stroke pump to remove moisture in the exhalation (FIG. 1).

The data output from the $^{13}$CO$_2$ analyzer were incorporated into a personal computer (Apple Power Macintosh 8500) after AD conversion. Using the data processing software Lab VIEW (National Instruments), data on 10 points at every 100 msec were added up and averaged at intervals of 5 sec and then converted into $^{13}$C atom %, $\Delta^{13}$C (‰) and CO$_2$ gas concentration (%), to thereby perform a continuous measurement $^{13}$C breath test. The converted data were displayed on the screen in real time and then stored in the hard disk. During the measurement, the rectum temperature in the rat was monitored and maintained at 37±0.5° C. using a body temperature controller for small animals (TR-100; Fine Science Tools Inc.). The CO$_2$ gas concentration in the sucked exhalation was maintained at 3±0.5%.

$\Delta^{13}$C (‰) was calculated from the $^{13}$C level in exhaled CO$_2$ at each time point ($^{13}$C t min) and the $^{13}$C level in standard CO$_2$ gas ($^{13}$C std) using the following formula:

$$\Delta^{13}C\ (‰)=[(^{13}C\ t\ min-^{13}C\ 0\ min)/^{13}C\ std]\times 1000$$

(2)-2 Oral Administration

Rats fasted overnight were fixed individually in a rat holder of a microwave irradiation apparatus without anesthesia. The exhalation was sucked with a stroke pump (variable stroke pump VS-500; Shibata Scientific Technology) at a rate of 100–300 ml/min and introduced directly into a flow cell in $^{13}$CO$_2$ Analyzer EX-130S (Japan Spectroscopic Co., Ltd.). A Perma Pure Drier (MD-050-12P; Perma Pure Inc.) was located between the rat holder and the stroke pump to remove moisture in the exhalation. When the CO$_2$ gas concentration was stabilized, the rat was once released from the rat holder, and then a specific amount of the labelled compound was administered into its stomach with a sound for oral administration.

The data output from the $^{13}$CO$_2$ analyzer were incorporated into a personal computer (Apple Power Macintosh 8500) after AD conversion. Using the data processing software Lab VIEW (National Instruments), data on 10 points at every 100 msec were added up and averaged at intervals of 5 sec and then converted into $^{13}$C atom %, $\Delta^{13}$C (‰) and CO$_2$ gas concentration (%), to thereby perform a continuous measurement $^{13}$C breath test. The converted data were displayed on the screen in real time and then stored in the hard disk.

$\Delta^{13}$C (‰) was calculated by the formula described above.

EXAMPLE 2

1-$^{13}$C-Galactose Breath Test

1-$^{13}$C-galactose (purchased from ICON) dissolved in physiological saline was administered to healthy rats (8-week-old; total bilirubin value≦0.5 mg/dl; n=3) and rats with acute hepatitis (8-week-old; total bilirubin value≧2.8 mg/dl; n=3) from the femoral vein at a dose of 100 mg/kg. Then, degrees of increase of $^{13}$C levels in exhaled CO$_2$ ($\Delta^{13}$C (‰)) were measured according to the method described in Example 1.

$\Delta^{13}$C values (‰) continued increasing up to 20 min after the administration of 1-$^{13}$C-galactose in both the healthy and the hepatitic rats (FIG. 2).

The $\Delta^{13}$C value (‰) at 20 min after the administration was 12.68±6.25‰ in the hepatitic rats, while the value was 42.43±3.75‰ in the healthy rats. Thus, the value in the hepatitis rats was very significantly (p<0.01 (ANOVA with Fischer LSD)) lower than that in the healthy rats.

The slope of increase of $\Delta^{13}$C values (‰) from 10 to 20 min after the administration was 6.31±8.22‰/10 min in the hepatitic rats, while the slope was 25.73±0.66‰/10 min in the healthy rats. Thus, the slope in the hepatitic rats was significantly (p<0.05 (ANOVA with Fischer LSD)) smaller than that in the healthy rats.

Accordingly, it is possible to detect a liver function disorder from the $\Delta^{13}$C value (‰) at a specific time after administration of 1-$^{13}$C-galactose or the slope of increase of $\Delta^{13}$C values (‰) after the administration.

EXAMPLE 3

1-$^{13}$C-Glucose Breath Test

1-$^{13}$C-glucose (purchased from CIL) dissolved in physiological saline was administered to healthy rats (8-week-old;

total bilirubin value≦0.6 mg/dl; n=4) and rats with acute hepatitis (8-week-old; total bilirubin value>3 mg/dl; n=4) from the femoral vein at a dose of 100 mg/kg. Then, degrees of increase of $^{13}C$ levels in exhaled $CO_2$ ($\Delta^{13}C$ (‰)) were measured according to the method described in Example 1.

$\Delta^{13}C$ values (‰) continued increasing up to 20 min after the administration of 1-$^{13}C$-glucose in both the healthy and the hepatitic rats (FIG. 3).

The $\Delta^{13}C$ value (‰) at 5 min after the administration was 48.90±2.97‰ in the hepatitic rats, while the value was 39.37±4.02‰ in the healthy rats. Thus, the value in the hepatitis rats was significantly (p<0.05 (ANOVA with Fischer LSD)) higher than that in the healthy rats.

The slope of increase of $\Delta^{13}C$ values (‰) from 2 to 5 min after the administration was 33.89±2.26‰/3 min in the hepatitic rats, while the slope was 23.97±2.03‰/3 min in the healthy rats. Thus, the slope in the hepatitic rats was very significantly (p<0.01 (ANOVA with Fischer LSD)) greater than that in the healthy rats.

Accordingly, it is possible to detect a liver function disorder from the $\Delta^{13}C$ value (‰) at a specific time after administration of 1-$^{13}C$-glucose or the slope of increase of $\Delta^{13}C$ values (‰) after the administration.

EXAMPLE 4

3 $^{13}C$-Glucose Breath Test

3-$^{13}C$-glucose (purchased from ICON) dissolved in physiological saline was administered to healthy rats (8-week-old; total bilirubin value≦0.6 mg/dl; n=4) and rats with acute hepatitis (8-week-old; total bilirubin value≧2.1 mg/dl; n=4) from the femoral vein at a dose of 100 mg/kg. Then, degrees of increase of $^{13}C$ levels in exhaled $CO_2$ ($\Delta^{13}C$ (‰)) were measured according to the method described in Example 1.

$\Delta^{13}C$ values (‰) continued increasing up to 20 min after the administration of 3-$^{13}C$-glucose in both the healthy and the hepatitic rats (FIG. 4).

The $\Delta^{13}C$ value (‰) at 5 min after the administration was 60.47±5.02‰ in the hepatitic rats, while the value was 46.09±5.67‰ in the healthy rats. Thus, the value in the hepatitic rats was significantly (p<0.05 (ANOVA with Fischer LSD)) higher than that in the healthy rats.

The slope of increase of $\Delta^{13}C$ values (‰) from 2 to 5 min after the administration was 50.99±3.66‰/3 min in the hepatitic rats, while the slope was 37.44±4.31‰/3 min in the healthy rats. Thus, the slope in the hepatitic rats was very significantly (p<0.01 (ANOVA with Fischer LSD)) greater than that in the healthy rats.

Accordingly, it is possible to detect a liver function disorder from the $\Delta^{13}C$ value (‰) at a specific time after administration of 3-$^{13}C$-glucose or the slope of increase of $\Delta^{13}C$ values (‰) after the administration.

EXAMPLE 5

U-$^{13}C$-Starch Breath Test

U-$^{13}C$-starch (purchased from Chlorella Industry) dissolved in physiological saline was administered orally to healthy rats (8-week-old; total bilirubin value=0.4 mg/dl; n=4) and rats with acute hepatitis (8-week-old; total bilirubin value>3 mg/dl; n=4) at a dose of 30 mg/kg. Then, degrees of increase of $^{13}C$ levels in exhaled $CO_2$ ($\Delta^{13}C$ (‰)) were measured according to the method described in Example 1.

$\Delta^{13}C$ values (‰) continued increasing up to 20 min after the administration of U-$^{13}C$-starch in both the healthy and the hepatitic rats (FIG. 5).

The $\Delta^{13}C$ value (‰) at 20 min after the administration was 116.18±27.12‰ in the hepatitic rats, while the value was 175.61±15.36‰ in the healthy rats. Thus, the value in the hepatitic rats was significantly (p<0.05 (ANOVA with Fischer LSD)) lower than that in the healthy rats.

Accordingly, it is possible to detect a liver function disorder from the $\Delta^{13}C$ value (‰) at a specific time after administration of U-$^{13}C$-starch.

EXAMPLE 6

1-$^{13}C$-Arginine Breath Test

1-$^{13}C$-arginine (purchased from ICON) dissolved in physiological saline was administered to healthy rats (8-week-old; total bilirubin value≦0.5 mg/dl; n=4) and rats with acute hepatitis (8-week-old; total bilirubin value>3 mg/dl; n=4) from the femoral vein at a dose of 50 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) continued increasing up to about 10 min after administration of 1-$^{13}C$-arginine. Thereafter, the value remained almost constant up to 20 min after the administration. On the other hand, in the hepatitic rats, $\Delta^{13}C$ value (‰) continued increasing up to 20 min after the administration (FIG. 6).

The $\Delta^{13}C$ value (‰) at 10 min after the administration was 62.55±4.93‰ in the hepatitic rats, while the value was 145.69±6.11‰ in the healthy rats. Thus, the value in the hepatitic rats was very significantly (p<0.0001 (ANOVA with Fischer LSD)) lower than that in the healthy rats.

The slope of increase of $\Delta^{13}C$ values (‰) from 4 to 9 min after the administration was 22.16±2.64‰/5 min in the hepatitic rats, while the slope was 56.67±4.22‰/5 min in the healthy rats. Thus, the slope in the hepatitic rats was very significantly (p<0.0001 (ANOVA with Fischer LSD)) smaller than that in the healthy rats.

Accordingly, it is possible to detect a liver function disorder from the $\Delta^{13}C$ value (‰) at a specific time after administration of 1-$^{13}C$-arginine or the slope of increase of $\Delta^{13}C$ values (‰) after the administration.

EXAMPLE 7

1-$^{13}C$-Histidine Breath Test

1-$^{13}C$-histidine (purchased from ICON) dissolved in physiological saline was administered to healthy rats (8-week-old; total bilirubin value≦0.5 mg/dl; n=4) and rats with acute hepatitis (8-week-old; total bilirubin value>4 mg/dl; n=4) from the femoral vein at a dose of 30 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) continued increasing up to about 17 min after administration of 1-$^{13}C$-histidine. Thereafter, the value remained almost constant up to 20 min after the administration. On the other hand, in the hepatitic rats, $\Delta^{13}C$ value (‰) continued increasing up to 20 min after the administration (FIG. 7).

The $\Delta^{13}C$ value (‰) at 15 min after the administration was 14.20±4.57‰ in the hepatitic rats, while the value was 90.01±18.15‰ in the healthy rats. Thus, the value in the hepatitic rats was very significantly (p<0.001 (ANOVA with Fischer LSD)) lower than that in the healthy rats.

The slope of increase of $\Delta^{13}C$ values (‰) from 5 to 10 min after the administration was 4.68±1.47‰/5 min in the hepatitic rats, while the slope was 43.76±10.84‰/5 min in the healthy rats. Thus, the slope in the hepatitic rats was very significantly (p<0.001 (ANOVA with Fischer LSD)) smaller than that in the healthy rats.

Accordingly, it is possible to detect a liver function disorder from the $\Delta^{13}C$ value (‰) at a specific time after administration of 1-$^{13}C$-histidine or the slope of increase of $\Delta^{13}C$ values (‰) after the administration.

EXAMPLE 8

1,2-$^{13}C$-Ornithine Breath Test 1,2-$^{13}C$-ornithine hydrochloride (purchased from ICON) dissolved in physiological saline was administered to healthy rats (8-week-old; total bilirubin value<0.5 mg/dl; n=4) and rats with acute hepatitis (8-week-old; total bilirubin value≧2.2 mg/dl; n=4) from the femoral vein at a dose of 20 mg/kg. Then, degrees of increase of $^{13}C$ levels in exhaled $CO_2$ ($\Delta^{13}C$ (‰) were measured according to the method described in Example 1.

In the healthy rats, $\Delta^{13}C$ value (‰) continued increasing up to about 20 min after administration of 1,2-$^{13}C$-ornithine hydrochloride. On the other hand, in the hepatitic rats, $\Delta^{13}C$ value (‰) sharply increased up to about 3 min after the administration, but thereafter increased gradually up to 20 min after the administration (FIG. 8).

The $\Delta^{13}C$ value (‰) at 15 min after the administration was 102.00±3.42‰ in the hepatitic rats, while the value was 137.37±10.79‰ in the healthy rats. Thus, the value in the hepatitic rats was very significantly (p<0.01 (ANOVA with Fischer LSD)) lower than that in the healthy rats.

The slope of increase of $\Delta^{13}C$ values (‰) from 4 to 9 min after the administration was 13.27±4.77‰/5 min in the hepatitic rats, while the slope was 39.92±3.91‰/5 min in the healthy rats. Thus, the slope in the hepatitic rats was very significantly (p<0.001 (ANOVA with Fischer LSD)) smaller than that in the healthy rats.

Accordingly, it is possible to detect a liver function disorder from the $\Delta^{13}C$ value (‰) at a specific time after administration of 1,2-$^{13}C$-ornithine hydrochloride or the slope of increase of $\Delta^{13}C$ values (‰) after the administration.

EXAMPLE 9

1-$^{13}C$-Valine Breath Test

1-$^{13}C$-valine (purchased from mass Trace) dissolved in physiological saline was administered to healthy rats (8-week-old; total bilirubin value≦0.6 mg/dl; n=4) and rats with acute hepatitis (8-week-old; total bilirubin value>3.5 mg/dl; n=4 from the femoral vein at a dose of 20 mg/kg. Then, degrees of increase of $^{13}C$ levels in exhaled $CO_2$ ($\Delta^{13}C$ (‰)) were measured according to the method described in Example 1.

$\Delta^{13}C$ values (‰) continued increasing up to 20 min after administration of 1-$^{13}C$-valine in both the healthy and the hepatitic rats (FIG. 9).

The $\Delta^{13}C$ value (‰) at 8 min after the administration was 34.65±6.08‰ in the hepatitic rats, while the value was 54.4±4.05‰ in the healthy rats. Thus, the value in the hepatitic rats was very significantly (p<0.01 (ANOVA with Fischer LSD)) lower than that in the healthy rats.

The slope of increase of $\Delta^{13}C$ values (‰) from 15 to 20 min after the administration was 4.3±1.38‰/5 min in the hepatitic rats, while the slope was −1.22±1.85‰/5 min in the healthy rats. Thus, the slope in the hepatitic rats was very significantly (p<0.01 (ANOVA with Fischer LSD)) greater than that in the healthy rats.

Accordingly, it is possible to detect a liver function disorder from the $\Delta^{13}C$ value (‰) at a specific time after administration of 1-$^{13}C$-valine or the slope of increase of $^{13}C$ values (‰) after the administration.

EXAMPLE 10

1-$^{13}C$-Lysine Breath Test

1-$^{13}C$-lysine hydrochloride (purchased from mass Trace) dissolved in physiological saline was administered to healthy rats (7-week-old; total bilirubin value≦0.7 mg/dl; n=4) and rats with acute hepatitis (7-week-old; total bilirubin value>3.5 mg/dl; n=4) from the femoral vein at a dose of 50 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) sharply increased up to about 10 min after administration of 1-$^{13}C$-lysine hydrochloride, and then remained almost constant up to about 15 min. Thereafter, the value began to decrease gradually up to 20 min after the administration. On the other hand, in the hepatitic rats, $\Delta^{13}C$ value (‰) continued increasing up to 20 min after the administration (FIG. 10).

The $\Delta^{13}C$ value (‰) at 10 min after the administration was 51.53±34.60‰ in the hepatitic rats, while the value was 138.29±9.76‰ in the healthy rats. Thus, the value in the hepatitic rats was very significantly (p<0.01 (ANOVA with Fischer LSD)) lower than that in the healthy rats.

The slope of increase of $\Delta^{13}C$ values (‰) from 3 to 8 min after the administration was 31.83±21.00‰/5 min in the hepatitic rats, while the slope was 86.41±9.63‰/5 min in the healthy rats. Thus, the slope in the hepatitic rats was very significantly (p<0.01 (ANOVA with Fischer LSD)) smaller than that in the healthy rats.

Accordingly, it is possible to detect a liver function disorder from the $\Delta^{13}C$ value (‰) at a specific time after administration of 1-$^{13}C$-lysine hydrochloride or the slope of increase of $\Delta^{13}C$ values (‰) after the administration.

EXAMPLE 11

1-$^{13}C$-Serine Breath Test

1-$^{13}C$-serine (purchased from ICON) dissolved in physiological saline was administered to healthy rats (8-week-old; total bilirubin value≦0.6 mg/dl; n=4) and rats with acute hepatitis (8-week-old; total bilirubin value>3 mg/dl; n=3) from the femoral vein at a dose of 50 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) sharply increased up to about 8 min after administration of 1-$^{13}C$-serine, and then remained almost constant up to about 15 min. Thereafter, the value began to decrease gradually up to 20 min after the administration. On the other hand, in the hepatitic rats, $\Delta^{13}C$ value (‰) continued increasing up to 20 min after the administration (FIG. 11).

The $\Delta^{13}C$ value (‰) at 2 min after the administration was 9.92±1.59‰ in the hepatitic rats, while the value was 28.42±5.43‰ in the healthy rats. Thus, the value in the hepatitic rats was very significantly (p<0.01 (ANOVA with Fischer LSD)) lower than that in the healthy rats.

The slope of increase of $\Delta^{13}C$ values (‰) from 10 to 20 min after the administration was 20.68±4.86‰/10 min in the hepatitic rats, while the slope was −8.81±4.16‰/10 min in the healthy rats. Thus, the slope in the hepatitic rats was very significantly (p<0.001 (ANOVA with Fischer LSD)) greater than that in the healthy rats.

Accordingly, it is possible to detect a liver function disorder from the $\Delta^{13}C$ value (‰) at a specific time after administration of 1-$^{13}$C-serine or the slope of increase of $\Delta^{13}C$ values (‰) after the administration.

EXAMPLE 12

1-$^{13}$C-Threonine Breath Test

1-$^{13}$C-threonine (purchased from mass Trace) dissolved in physiological saline was administered to healthy rats (7-week-old; total bilirubin value≦0.6 mg/dl; n=4) and rats with acute hepatitis (7-week-old; total bilirubin value>3 mg/dl; n=4) from the femoral vein at a dose of 50 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) sharply increased up to about 8 min after administration of 1-$^{13}$C-threonine, but remained almost constant thereafter up to 20 min. On the other hand, in the hepatitic rats, $\Delta^{13}C$ value (‰)) continued increasing up to 20 min after the administration (FIG. 12).

The $\Delta^{13}C$ value (‰) at 8 min after the administration was 20.56±9.62‰ in the hepatitic rats, while the value was 92.92±36.36‰ in the healthy rats. Thus, the value in the hepatitic rats was significantly (p<0.05 (ANOVA with Fischer LSD)) lower than that in the healthy rats.

The slope of increase of $\Delta^{13}C$ values (‰) from 10 to 20 min after the administration was 14.65±4.11‰/10 min in the hepatitic rats, while the slope was 0.01±5.79‰/10 min in the healthy rats. Thus, the slope in the hepatitic rats was significantly (p<0.05 (ANOVA with Fischer LSD)) greater than that in the healthy rats.

Accordingly, it is possible to detect a liver function disorder from the $\Delta^{13}C$ value (‰) at a specific time after administration of 1-$^{13}$C-threonine or the slope of increase of $\Delta^{13}C$ values (‰) after the administration.

EXAMPLE 13

1-$^{13}$C-Cysteine Breath Test

1-$^{13}$C-cysteine (purchased from ICON) dissolved in physiological saline was administered to healthy rats (8-week-old; total bilirubin value≦0.5 mg/dl; n=4) and rats with acute hepatitis (8-week-old; total bilirubin value≧2.1 mg/dl; n=2) from the femoral vein at a dose of 20 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) sharply increased up to about 4 min after administration of 1-$^{13}$C-cysteine, but gradually decreased thereafter up to 20 min. On the other hard, in the hepatitic rats, $\Delta^{13}C$ value (‰) increased up to about 7 min after the administration, but gradually decreased thereafter up to 20 min (FIG. 13).

The $\Delta^{13}C$ value (‰) at 2 min after the administration was 30.11‰ in the hepatitic rats, while the value was 71.93±13.52‰ in the healthy rats. Thus, the value in the hepatitis rats was significantly (p<0.05 (ANOVA with Fischer LSD)) lower than that in the healthy rats.

Accordingly, it is possible to detect a liver function disorder from the $\Delta^{13}C$ value (‰) at a specific time after administration of 1-$^{13}$C-cysteine.

EXAMPLE 14

1-$^{13}$C-Glutamic Acid Breath Test

1-$^{13}$C-glutamic acid (purchased from mass Trace) dissolved in physiological saline was administered to healthy rats (8-week-old; total bilirubin value≦0.6 mg/dl; n=2) and rats with acute hepatitis (8-week-old; total bilirubin value>4 mg/dl; n=4) from the femoral vein at a dose of 10 mg/kg. Then, degrees of increase of $^{13}C$ levels in exhaled $CO_2$ ($\Delta^{13}C$ (‰)) were measured according to the method described in Example 1.

$\Delta^{13}C$ values (‰)) sharply increased up to about 4 min after administration of 1-$^{13}$C-glutamic acid in both the healthy and the hepatitic rats, but gradually decreased thereafter up to 20 min (FIG. 14).

The $\Delta^{13}C$ value (‰)) at 3 min after the administration was 175.98±20.94‰ in the hepatitic rats, while the value was 236.10‰ in the healthy rats. Thus, the value in the hepatitic rats was significantly (p<0.05 (ANOVA with Fischer LSD)) lower than that in the healthy rats.

Accordingly, it is possible to detect a liver function disorder from the $\Delta^{13}C$ value (‰) at a specific time after administration of 1-$^{13}$C-glutamic acid.

EXAMPLE 15

1-$^{13}$C-Proline Breath Test

1-$^{13}$C-proline (purchased from mass Trace) dissolved in physiological saline was administered to healthy rats (8-week-old; total bilirubin value<0.5 mg/dl; n=4) and rats with acute hepatitis (8-week-old; total bilirubin value≧1.5 mg/dl; n=4) from the femoral vein at a dose of 20 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) increased up to about 9 min after administration of 1-$^{13}$C-proline, but decreased gradually thereafter up to 20 min. On the other hand, in the hepatitic rats, $\Delta^{13}C$ value (‰) continued increasing up to 20 min after the administration (FIG. 15).

The slope of increase of $\Delta^{13}C$ values (‰) from 15 to 20 min after the administration was −0.25±2.93‰/5 min in the hepatitic rats, while the slope was −8.91±1.18‰/5 min in the healthy rats. Thus, the slope in the hepatitic rats was very significantly (p<0.01 (ANOVA with Fischer LSD)) greater than that in the healthy rats.

Accordingly, it is possible to detect a liver function disorder from the slope of increase of $\Delta^{13}C$ values (‰) after administration of 1-$^{13}$C-proline.

EXAMPLE 16

1-$^{13}$C-Tryptophan Breath Test

1-$^{13}$C-tryptophan (purchased from mass Trace) dissolved in physiological saline was administered to healthy rats (9-week-old; total bilirubin value≦0.5 mg/dl; n=4) and rats with acute hepatitis (9-week-old; total bilirubin value≧4 mg/dl; n=4) from the femoral vein at a dose of 10 mg/kg. Then, degrees of increase of $^{13}C$ levels in exhaled $CO_2$ ($\Delta^{13}C$ (‰)) were measured according to the method described in Example 1.

The $\Delta^{13}C$ value (‰) at 5 min after administration of 1-$^{13}C$-tryptophan was 1.49±0.51‰ in the hepatitic rats, while the value was 4.78±2.04‰ in the healthy rats. Thus, the value in the hepatitic rats was significantly (p<0.05 (ANOVA with Fischer LSD)) lower than that in the healthy rats.

Accordingly, it is possible to detect a liver function disorder from the $\Delta^{13}C$ value (‰) at a specific time after administration of 1-$^{13}C$-tryptophan.

EXAMPLE 17

1-$^{13}C$-Isoleucine Breath Test

1-$^{13}C$-isoleucine (purchased from mass Trace) dissolved in physiological saline was administered to healthy rats (8-week-old; total bilirubin value≦0.5 mg/dl; n=4) and rats with acute hepatitis (8-week-old; total bilirubin value>4 mg/dl; n=4) from the femoral vein at a dose of 20 mg/kg. Then, degrees of increase of $^{13}C$ levels in exhaled $CO_2$ ($\Delta^{13}C$ (‰)) were measured according to the method described in Example 1.

The slope of increase of $\Delta^{13}C$ values (‰) from 10 to 20 min after the administration was 27.99±2.70‰/10 min in the hepatitic rats, while the slope was 11.28±3.44‰/10 min in the healthy rats. Thus, the slope in the hepatitic rats was very significantly (p<0.001 (ANOVA with Fischer LSD)) greater than that in the healthy rats.

Accordingly, it is possible to detect a liver function disorder from the slope of increase of $\Delta^{13}C$ values (‰) after administration of 1-$^{13}C$-isoleucine.

EXAMPLE 18

1,1-$^{13}C$-Cystine Breath Test 1,1-$^{13}C$-cystine (purchased from mass Trace) suspended in 0.5% aqueous solution of sodium carboxymethylcellulose was administered orally to healthy rats (9-week-old; total bilirubin value≦0.6 mg/dl; n=4) and rats with acute hepatitis (9-week-old; total bilirubin value>4.5 mg/dl; n=4) at a dose of 45 mg/kg. Then, degrees of increase of $^{13}C$ levels in exhaled $CO_2$ ($\Delta^{13}C$ (‰)) were measured according to the method described in Example 1.

$\Delta^{13}C$ values (‰) continued increasing up to 30 min after administration of 1,1-$^{13}C$-cystine in both the healthy and the hepatitic rats (FIG. 16).

The $\Delta^{13}C$ value (‰) at 30 min after the administration was 58.36±13.51‰ in the hepatitic rats, while the value was 146.48±19.34‰ in the healthy rats. Thus, the value in the hepatitic rats was very significantly (p<0.001 (ANOVA with Fischer LSD)) lower than that in the healthy rats.

The slope of increase of $\Delta^{13}C$ values (‰) from 5 to 10 min after the administration was 10.93±3.83‰/5 min in the hepatitic rats, while the slope was 38.11±9.58‰/5 min in the healthy rats. Thus, the slope in the hepatitic rats was very significantly (p<0.01 (ANOVA with Fischer LSD)) smaller than that in the healthy rats.

Accordingly, it is possible to detect a liver function disorder from the $\Delta^{13}C$ value (‰) at a specific time after administration of 1,1-$^{13}C$-cystine or the slope of increase of $^{13}C$ values (‰) after the administration.

EXAMPLE 19

1-$^{13}C$-Aspartic Acid Breath Test

1-$^{13}C$-aspartic acid (purchased from mass Trace) dissolved in physiological saline was administered to healthy rats (8-week-old; total bilirubin value≦0.4 mg/dl; n=4) and rats with acute hepatitis (8-week-old; total bilirubin value≧2.8 mg/dl; n=4) from the femoral vein at a dose of 10 mg/kg. Then, degrees of increase of $^{13}C$ levels in exhaled $CO_2$ ($\Delta^{13}C$ (‰)) were measured according to the method described in Example 1.

The $\Delta^{13}C$ value (‰) at 2 min after the administration was 139.25±2.53‰ in the hepatitic rats, while the value was 158.35±8.54‰ in the healthy rats. Thus, the value in the hepatitic rats was very significantly (p<0.01 (ANOVA with Fischer LSD)) lower than that in the healthy rats.

Accordingly, it is possible to detect a liver function disorder from the $\Delta^{13}C$ value (‰) at a specific time after administration of 1-$^{13}C$-aspartic acid.

EXAMPLE 20

1-$^{13}C$-Lactic Acid Breath Test

1-$^{13}C$-sodium lactate (purchased from mass Trace) dissolved in physiological saline was administered to healthy rats (8-week-old; total bilirubin value≦0.6 mg/dl; n=4) and rats with acute hepatitis (8-week-old; total bilirubin value>3.5 mg/dl; n=4) from the femoral vein at a dose of 10 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) sharply increased up to about 2 min after administration of 1-$^{13}C$-sodium lactate, but thereafter decreased gradually up to 20 min. On the other hand, in the hepatitic rats, $\Delta^{13}C$ value (‰) increased up to about 4 min after the administration, but thereafter decreased gradually up to 20 min (FIG. 17).

The $\Delta^{13}C$ value (‰) at 2 min after the administration was 76.07±5.56‰ in the hepatitic rats, while the value was 251.21±26.15‰ in the healthy rats. Thus, the value in the hepatitic rats was very significantly (p<0.0001 (ANOVA with Fischer LSD)) lower than that in the healthy rats.

The slope of increase of $\Delta^{13}C$ values (‰) from 1 to 2 min after the administration was 43.41±4.15‰/min in the hepatitic rats, while the slope was 171.16±22.39‰/min in the healthy rats. Thus, the slope in the hepatitic rats was very significantly (p<0.0001 (ANOVA with Fischer LSD)) smaller than that in the healthy rats.

Accordingly, it is possible to detect a liver function disorder from the $\Delta^{13}C$ value (‰) at a specific time after administration of 1-$^{13}C$-sodium lactate or the slope of increase of $\Delta^{13}C$ values (‰) after the administration.

EXAMPLE 21

3-$^{13}C$-Lactic Acid Breath Test

3-$^{13}C$-sodium lactate (purchased from mass Trace) dissolved in physiological saline was administered to healthy rats (10-week-old; total bilirubin value=0.3 mg/dl; n=3) and rats with acute hepatitis (10-week-old; total bilirubin value≧2.5 mg/dl; n=6) from the femoral vein at a dose of 50 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) sharply increased up to about 8 min after administration of 3-$^{13}C$-sodium lactate, but thereafter remained almost constant up to 20 min. On the other hand, in the hepatitic rats, $\Delta^{13}C$ value (‰) continued increasing up to 20 min after the administration (FIG. 18).

The $\Delta^{13}C$ value (‰) at 5 min after the administration was 55.42±10.84‰ in the hepatitic rats, while the value was 124.48±27.01‰ in the healthy rats. Thus, the value in the hepatitic rats was very significantly (p<0.01 (ANOVA with Fischer LSD)) lower than that in the healthy rats.

The slope of increase of $\Delta^{13}C$ values (‰) from 10 to 15 min after the administration was 19.15±9.20‰/5 min in the hepatitic rats, while the slope was 0.81±5.16‰/5 min in the healthy rats. Thus, the slope in the hepatitic rats was significantly (p<0.05 (ANOVA with Fischer LSD)) greater than that in the healthy rats.

Accordingly, it is possible to detect a liver function disorder from the $\Delta^{13}C$ value (‰) at a specific time after administration of 3-$^{13}$C-sodium lactate or the slope of increase of $\Delta^{13}C$ values (‰) after the administration.

EXAMPLE 22

1-$^{13}$C-Pyruvic Acid Breath Test

1-$^{13}$C-sodium pyruvate (purchased from ICON) dissolved in physiological saline was administered to healthy rats (8-week-old; total bilirubin values≦0.5 mg/dl; n=4) and rats with acute hepatitis (8-week-old; total bilirubin value>3 mg/dl; n=4) from the femoral vein at a dose of 20 mg/kg. Then, degrees of increase of $^{13}$C levels in exhaled $CO_2$ ($\Delta^{13}C$ (‰)) were measured according to the method described in Example 1.

In the healthy rats, $\Delta^{13}C$ value (‰) sharply increased up to about 4 min after administration of 1-$^{13}$C-sodium pyruvate, but thereafter decreased gradually up to 14 min. On the other hand, in the hepatitic rats, $\Delta^{13}C$ value (‰) sharply increased up to about 5 min after the administration, but thereafter decreased gradually up to 14 min (FIG. 19).

The $\Delta^{13}C$ value (‰) at 4 min after the administration was 234.23±33.66‰ in the hepatitic rats, while the value was 319.45±21.16‰ in the healthy rats. Thus, the value in the hepatitic rats was very significantly (p<0.01 (ANOVA with Fischer LSD)) lower than that in the healthy rats.

Accordingly, it is possible to detect a liver function disorder from the $\Delta^{13}C$ value (‰) at a specific time after administration of 1-$^{13}$C-sodium pyruvate.

EXAMPLE 23

3-$^{13}$C-Pyruvic Acid Breath Test

3-$^{13}$C-sodium pyruvate (purchased from ICON) dissolved in physiological saline was administered orally to healthy rats (8-week-old; total bilirubin value<0.5 mg/dl; n=4) and rats with acute hepatitis (8-week-old; total bilirubin value>3.5 mg/dl; n=4) at a dose of 20 mg/kg. Then, degrees of increase of $^{13}$C levels in exhaled $CO_2$ ($\Delta^{13}C$ (‰)) were measured according to the method described in Example 1.

In the healthy rats, $\Delta^{13}C$ value (‰) sharply increased up to about 7 min after administration of 3-$^{13}$C-sodium pyruvate, but thereafter remained almost constant up to 20 min. On the other hand, in the hepatitic rats, $\Delta^{13}C$ value (‰) sharply increased up to about 6 min after the administration, but thereafter increased gradually up to 20 min (FIG. 20).

The $\Delta^{13}C$ value (‰) at 7 min after the administration was 160.20±26.27‰ in the hepatitic rats, while the value was 226.58±26.56‰ in the healthy rats. Thus, the value in the hepatitic rats was significantly (p<0.05 (ANOVA with Fischer LSD)) lower than that in the healthy rats.

The slope of increase of $\Delta^{13}C$ values (‰) from 10 to 20 min after the administration was 26.35±3.06‰/10 min in the hepatitic rats, while the slope was −0.28±7.50‰/10 min in the healthy rats. Thus, the slope in the hepatitic rats was very significantly (p<0.01 (ANOVA with Fischer LSD)) greater than that in the healthy rats.

Accordingly, it is possible to detect a liver function disorder from the $\Delta^{13}C$ value (‰) at a specific time after administration of 3-$^{13}$C-sodium pyruvate or the slope of increase of $\Delta^{13}C$ values (‰) after the administration.

EXAMPLE 24

1,4-$^{13}$C-Succinic Acid Breath Test 1,4-$^{13}$C-succinic acid (purchased from ICON) dissolved in physiological saline was administered to healthy rats (10-week-old; total bilirubin value≦0.5 mg/dl; n=3) and rats with acute hepatitis (10-week-old; total bilirubin value>4 mg/dl; n=4) from the femoral vein at a dose of 4 mg/kg. Then, degrees of increase of $^{13}$C levels in exhaled $CO_2$ ($\Delta^{13}C$ (‰)) were measured according to the method described in Example 1.

$\Delta^{13}C$ values (‰) sharply increased up to 3 min after administration of 1,4-$^{13}$C-succinic acid in both the healthy and the hepatitic rats, but gradually decreased thereafter up to 20 min (FIG. 21).

The $\Delta^{13}C$ value (‰) at 7 min after the administration was 211.88±10.19‰ in the hepatitic rats, while the value was 236.60±5.93‰ in the healthy rats. Thus, the value in the hepatitic rats was significantly (p<0.05 (ANOVA with Fischer LSD)) lower than that in the healthy rats.

Accordingly, it is possible to detect a liver function disorder from the $\Delta^{13}C$ value (‰) at a specific time after administration of 1,4-$^{13}$C-succinic acid.

EXAMPLE 25

1,6-$^{13}$C-Citric Acid Breath Test 1,6-$^{13}$C-citric acid (purchased from ICON) dissolved in physiological saline was administered to healthy rats (8-week-old; total bilirubin values≦0.6 mg/dl; n=4) and rats with acute hepatitis (8-week-old; total bilirubin value>3 mg/dl; n=4) from the femoral vein at a dose of 5 mg/kg. Then, degrees of increase of $^{13}$C levels in exhaled $CO_2$ ($\Delta^{13}C$ (‰)) were measured according to the method described in Example 1.

The $\Delta^{13}C$ value (‰) at 15 min after administration of 1,6-$^{13}$C-citric acid was 66.70±1.10‰ in the hepatitic rats, while the value was 74.54±1.53‰ in the healthy rats. Thus, the value in the hepatitic rats was very significantly (p<0.001 (ANOVA with Fischer LSD)) lower than that in the healthy rats.

Accordingly, it is possible to detect a liver function disorder from the $\Delta^{13}C$ value (‰) at a specific time after administration of 1,6-$^{13}$C-citric acid.

EXAMPLE 26

1-$^{13}$C-Oleic Acid Breath Test

1-$^{13}$C-oleic acid (purchased from ICON) emulsified with Tween 20 (0.2%) and physiological saline was administered to healthy rats (total bilirubin value≦0.7 mg/dl; n=4) and rats with acute hepatitis (total bilirubin value≧2.4 mg/dl; n=4) from the femoral vein at a dose of 70 mg/kg. Then, degrees of increase of $^{13}$C levels in exhaled $CO_2$ ($\Delta^{13}C$ (‰)) were measured according to the method described in Example 1.

In the healthy rats, $\Delta^{13}C$ value (‰) continued increasing up to 20 min after administration of 1-$^{13}$C-oleic acid. On the other hand, in the hepatitic rats, $\Delta^{13}C$ value (‰) increased up to about 8 min after the administration, but thereafter remained almost constant up to 20 min (FIG. 22).

The $\Delta^{13}C$ value (‰) at 20 min after the administration was 89.80±10.44‰ in the hepatitic rats, while the value was 119.81±2.14‰ in the healthy rats. Thus, the value in the hepatitic rats was very significantly ($p<0.01$ (ANOVA with Fischer LSD)) lower than that in the healthy rats.

The slope of increase of $\Delta^{13}C$ values (‰) from 10 to 20 min after the administration was −1.79±1.58‰/10 min in the hepatitic rats, while the slope was 18.22±2.94‰/10 min in the healthy rats. Thus, the slope in the hepatitic rats was very significantly ($p<0.0001$ (ANOVA with Fischer LSD)) smaller than that in the healthy rats.

Accordingly, it is possible to detect a liver function disorder from the $\Delta^{13}C$ value (‰) at a specific time after administration of 1-$^{13}C$-oleic acid or the slope of increase of $\Delta^{13}C$ values (‰) after the administration.

EXAMPLE 27

1-$^{13}C$-Octanoic Acid Breath Test

1-$^{13}C$-octanoic acid (purchased from mass Trace) emulsified with Tween 20 (0.2%) and physiological saline was administered to healthy rats (total bilirubin value≦0.7 mg/dl; n=4) and rats with acute hepatitis (total bilirubin value>2.5 mg/dl; n=4) from the femoral vein at a dose of 30 mg/kg. Then, degrees of increase of $^{13}C$ levels in exhaled $CO_2$ ($\Delta^{13}C$ (‰)) were measured according to the method described in Example 1.

$\Delta^{13}C$ values (‰) sharply increased up to about 5 min after administration of 1-$^{13}C$-octanoic acid in both the healthy and the hepatitic rats, but thereafter decreased gradually up to 20 min (FIG. 23).

The $\Delta^{13}C$ value (‰) at 2 min after the administration was 12.71±2.00‰ in the hepatitic rats, while the value was 8.37±1.42‰ in the healthy rats. Thus, the value in the hepatitic rats was significantly ($p<0.05$ (ANOVA with Fischer LSD)) higher than that in the healthy rats.

The slope of increase of $\Delta^{13}C$ values (‰) from 10 to 20 min after the administration was −5.48±1.33‰/10 min in the hepatitic rats, while the slope was −2.21±0.29‰/10 min in the healthy rats. Thus, the slope in the hepatitic rats was very significantly ($p<0.01$ (ANOVA with Fischer LSD)) smaller than that in the healthy rats.

Accordingly, it is possible to detect a liver function disorder from the $\Delta^{13}C$ value (‰) at a specific time after administration of 1-$^{13}C$-octanoic acid or the slope of increase of $\Delta^{13}C$ values (‰) after the administration.

EXAMPLE 28

1-$^{13}C$-Palmitic Acid Breath Test

1-$^{13}C$-palmitic acid (purchased from mass Trace) emulsified with Tween 20 (0.4%) and physiological saline was administered to healthy rats (total bilirubin value≦0.7 mg/dl; n=4) and rats with acute hepatitis (total bilirubin value≧4 mg/dl; n=4) from the femoral vein at a dose of 50 mg/kg. Then, degrees of increase of $^{13}C$ levels in exhaled $CO_2$ ($\Delta^{13}C$ (‰)) were measured according to the method described in Example 1.

The $\Delta^{13}C$ value (‰) at 15 min after the administration was 12.22±0.36‰ in the hepatitic rats, while the value was 13.67±0.41‰ in the healthy rats. Thus, the value in the hepatitic rats was very significantly ($p<0.01$ (ANOVA with Fischer LSD)) lower than that in the healthy rats.

Accordingly, it is possible to detect a liver function disorder from the $\Delta^{13}C$ value (‰) at a specific time after administration of 1-$^{13}C$-palmitic acid.

EXAMPLE 29

1-$^{13}C$-Acetic Acid Breath Test

1-$^{13}C$-acetic acid (purchased from mass Trace) dissolved in physiological saline was administered to healthy rats (total bilirubin values≦0.8 mg/dl; n=4) and rats with acute hepatitis (total bilirubin value>2 mg/dl; n=4) from the femoral vein at a dose of 10 mg/kg. Then, degrees of increase of $^{13}C$ levels in exhaled $CO_2$ ($\Delta^{13}C$ (‰)) were measured according to the method described in Example 1.

The $\Delta^{13}C$ value (‰) at 20 min after the administration was 144.05±3.81‰ in the hepatitic rats, while the value was 153.55±1.94‰ in the healthy rats. Thus, the value in the hepatitic rats was very significantly ($p<0.01$ (ANOVA with Fischer LSD)) lower than that in the healthy rats.

Accordingly, it is possible to detect a liver function disorder from the $\Delta^{13}C$ value (‰) at a specific time after administration of 1-$^{13}C$-acetic acid.

EXAMPLE 30

1,1,1-$^{13}C$-Trioctanoin Breath Test 1,1,1-$^{13}C$-trioctanoin (purchased from mass Trace) emulsified with Tween 20 (0.2%) and physiological saline was administered to healthy rats (total bilirubin value≦0.6 mg/dl; n=4) and rats with acute hepatitis (total bilirubin value≧3.5 mg/dl; n=4) from the femoral vein at a dose of 30 mg/kg. Then, degrees of increase of $^{13}C$ levels in exhaled $CO_2$ ($\Delta^{13}C$ (‰)) were measured according to the method described in Example 1.

In the healthy rats, $\Delta^{13}C$ value (‰) sharply increased up to about 6 min after administration of 1,1,1-$^{13}C$-trioctanoin, but thereafter increased gradually up to 20 min. On the other hand, in the hepatitic rats, $\Delta^{13}C$ value (‰) continued increasing gradually up to 20 min (FIG. 24).

The $\Delta^{13}C$ value (‰) at 6 min after the administration was 15.78±10.78‰ in the hepatitic rats, while the value was 64.06±5.69‰ in the healthy rats. Thus, the value in the hepatitic rats was very significantly ($p<0.001$ (ANOVA with Fischer LSD)) lower than that in the healthy rats.

The slope of increase of $\Delta^{13}C$ values (‰) from 2 to 5 min after the administration was 10.14±7.59‰/3 min in the hepatitic rats, while the slope was 49.29±4.97‰/3 min in the healthy rats. Thus, the slope in the hepatitic rats was very significantly ($p<0.001$ (ANOVA with Fischer LSD)) smaller than that in the healthy rats.

Accordingly, it is possible to detect a liver function disorder from the $\Delta^{13}C$ value (‰) at a specific time after administration of 1,1,1-$^{13}C$-trioctanoin or the slope of increase of $\Delta^{13}C$ values (‰) after the administration.

EXAMPLE 31

2-$^{13}C$-Glycerol Breath Test

2-$^{13}C$-glycerol (purchased from CIL) dissolved in physiological saline was administered to healthy rats (total bilirubin value≦0.5 mg/dl; n=4) and rats with acute hepatitis (total bilirubin value>3.5 mg/dl; n=4) from the femoral vein at a dose of 50 mg/kg. Then, degrees of increase of $^{13}C$ levels in exhaled $CO_2$ ($\Delta^{13}C$ (‰)) were measured according to the method described in Example 1.

$\Delta^{13}C$ value (‰) continued increasing up to 20 min after administration of 2-$^{13}$C-glycerol in both the healthy and the hepatitic rats (FIG. 25).

The $\Delta^{13}C$ value (‰) at 20 min after the administration was 78.69±15.82‰ in the hepatitic rats, while the value was 53.35±3.3‰ in the healthy rats. Thus, the value in the hepatitic rats was significantly (p<0.05 (ANOVA with Fischer LSD)) higher than that in the healthy rats.

The slope of increase of $\Delta^{13}C$ values (‰) from 10 to 20 min after the administration was 39.51±5.06‰/10 min in the hepatitic rats, while the slope was 24.06±2.13‰/10 min in the healthy rats. Thus, the slope in the hepatitic rats was very significantly (p<0.01 (ANOVA with Fischer LSD)) greater than that in the healthy rats.

Accordingly, it is possible to detect a liver function disorder from the $\Delta^{13}C$ value (‰) at a specific time after administration of 2-$^{13}$C-glycerol or the slope of increase of $\Delta^{13}C$ values (‰) after the administration.

Formulation Example 1

Injection 10 parts by weight of 1-$^{13}$C-galactose was dissolved in 90 parts by weight of physiological saline and sterilized by filtration with a Millipore filter. The filtrate was put into a vial and sealed to give an injection.

Formulation Example 2

Internal Liquid Agent 10 parts by weight of 1-$^{13}$C-glucose was dissolved in 90 parts by weight of distilled and de-ionized water (DDW) and sterilized by filtration with a Millipore filter. The filtrate was put into a vial and sealed to give an internal liquid agent.

Formulation Example 3

Injection 10 parts by weight of 1-$^{13}$C-arginine was dissolved in 90 parts by weight of physiological saline and sterilized by filtration with a Millipore filter. The filtrate was put into a vial and sealed to give an injection.

Formulation Example 4

Internal Liquid Agent 10 parts by weight of 1-$^{13}$C-histidine was dissolved in 90 parts by weight of DDW and sterilized by filtration with a Millipore filter. The filtrate was put into a vial and sealed to give an internal liquid agent.

Formulation Example 5

Injection 10 parts by weight of 1-$^{13}$C-sodium lactate was dissolved in 90 parts by weight of physiological saline and sterilized by filtration with a Millipore filter. The filtrate was put into a vial and sealed to give an injection.

Formulation Example 6

Internal Liquid Agent 10 parts by weight of 1-$^{13}$C-sodium pyruvate was dissolved in 90 parts by weight of DDW and sterilized by filtration with a Millipore filter. The filtrate was put into a vial and sealed to give an internal liquid agent.

Formulation Example 7

Injection 10 parts by weight of 1-$^{13}$C-oleic acid, 89 parts by weight of physiological saline and 1 part by weight of Polysorbate 80 (all sterilized in advance) were mixed aseptically and emulsified with a ultrasound homogenizer. The resultant emulsion was put into a vial and sealed to give an injection.

Formulation Example 8

Internal Liquid Agent 10 parts by weight of 1-$^{13}$C-acetic acid was dissolved in 90 parts by weight of DDW and sterilized by filtration with a Millipore filter. The filtrate was put into a vial and sealed to give an internal liquid agent.

Formulation Example 9

Injection 10 parts by weight of 1,1,1-$^{13}$C-trioctanoin, 89 parts by weight of physiological saline and 1 part by weight of Polysorbate 80 (all sterilized in advance) were mixed aseptically and emulsified with a ultrasound homogenizer. The resultant emulsion was put into a vial and sealed to give an injection.

Formulation Example 10

Internal Liquid Agent 10 parts by weight of 1,1,1-$^{13}$C-trioctanoin, 89 parts by weight of DDW and 1 part by weight of Tween 20 (all sterilized in advance) were mixed aseptically and emulsified with a ultrasound homogenizer. The resultant emulsion was put into a vial and sealed to give an internal liquid agent.

Formulation Example 11

Injection 10 parts by weight of 2-$^{13}$C-glycerol was dissolved in 90 parts by weight of physiological saline and sterilized by filtration with a Millipore filter. The filtrate was put into a vial and sealed to give an injection.

Formulation Example 12

Internal Liquid Agent 10 parts by weight of 2-$^{13}$C-glycerol was dissolved in 90 parts by weight of DDW and sterilized by filtration with a Millipore filter. The filtrate was put into a vial and sealed to give an internal liquid agent.

What is claimed is:

1. A diagnostic agent for liver function, comprising a compound labelled with $^{13}$C at least at one specific position selected from the group consisting of the following (a) to (f):
    (a) galactose, glucose or xylose labelled with $^{13}$C at least at one specific position or a starch composed of glucose units labelled with $^{13}$C at least at one specific position;
    (b) a polar amino acid excluding tyrosine, heterocyclic amino acid, isoleucine or valine labelled with $^{13}$C at least at one specific position;
    (c) a carboxylic acid constituting the glycolytic pathway of the citric acid cycle, labelled with $^{13}$C at least at one specific position;

(d) a fatty acid labelled with $^{13}C$ at least at one specific position;

(e) a glyceride labelled with $^{13}C$ at least at one specific position; and (f) glycerol labelled with $^{13}C$ at least at one specific position.

2. The diagnostic agent according to claim 1, wherein the polar amino acid is arginine, asparagine, aspartic acid, glutamine, glutamic acid, cysteine, cystine, glycine, lysine, serine, threonine or ornithine.

3. The diagnostic agent according to claim 1, wherein the heterocyclic amino acid is tryptophan, proline or histidine.

4. The diagnostic agent according to claim 1, wherein the carboxylic acid constituting the glycolytic pathway or the citric acid cycle is pyruvic acid, lactic acid, succinic acid or citric acid.

5. The diagnostic agent according to claim 1, wherein the fatty acid is acetic acid, linolic acid, linolenic acid, oleic acid, octanoic acid or palmitic acid.

6. The diagnostic agent according to claim 1, wherein the glyceride is trioctanoin, tripalmitin or triolein.

7. A method for diagnosing liver function, comprising administering to a subject a compound labelled with $^{13}C$ at least at one specific position selected from the group consisting of the following (a) to (f):

(a) galactose, glucose or xylose labelled with $^{13}C$ at least at one specific position or a starch composed of glucose units labelled with $^{13}C$ at least at one specific position;

(b) a polar amino acid excluding tyrosine, heterocyclic amino acid, isoleucine or valine labelled with $^{13}C$ at least at one specific position;

(c) a carboxylic acid constituting the glycolytic pathway of the citric acid cycle, labelled with $^{13}C$ at least at one specific position;

(d) a fatty acid labelled with $^{13}C$ at least at one specific position;

(e) a glyceride labelled with $^{13}C$ at least at one specific position; and (f) glycerol labelled with $^{13}C$ at least at one specific position;

measuring $^{13}C$ levels in the exhaled $CO_2$ for a specific period of time and comparing the degree of increase of $^{13}C$ level with that in healthy individuals.

8. The method according to claim 7, wherein the polar amino acid is arginine, asparagine, aspartic acid, glutamine, glutamic acid, cysteine, cystine, glycine, lysine, serine, threonine or ornithine.

9. The method according to claim 7, wherein the heterocyclic amino acid is tryptophan, proline or histidine.

10. The method according to claim 7, wherein the carboxylic acid constituting the glycolytic pathway or the citric acid cycle is pyruvic acid, lactic acid, succinic acid or citric acid.

11. The method according to claim 7, wherein the fatty acid is acetic acid, linolic acid, linolenic acid, oleic acid, octanoic acid or palmitic acid.

12. The method according to claim 7, wherein the glyceride is trioctanoin, tripalmitin or triolein.

* * * * *

UNITED STATES PATENT AND TRADEMARK OFFICE
CERTIFICATE OF CORRECTION

PATENT NO. : 6,071,245
DATED : October 1, 1998
INVENTOR(S) : Tadashi Kohno et al.

It is certified that error appears in the above-identified patent and that said Letters Patent is hereby corrected as shown below:

Column 20,
Line 56, please amend claim 1, as follows:
1. A diagnostic agent for liver function, comprising a compound labelled with $^{13}$C at least at one specific position selected from the group consisting of the following (a) to (f):
(a) galactose, glucose or xylose labelled with $^{13}$C at least at one specific position or a starch composed of glucose units labelled with $^{13}$C at least at one specific position;
(b) a polar amino acid excluding tyrosine, heterocyclic amino acid, isoleucine or valine labelled with $^{13}$C at least at one specific position;
(c) a carboxylic acid constituting the glycolytic pathway or the citric acid cycle, labelled with $^{13}$C at least at one specific position;
(d) a fatty acid labelled with $^{13}$C at least at one specific position;
(e) a glyceride labelled with $^{13}$C at least at one specific position; and
(f) glycerol labelled $^{13}$C at least at one specific position.

Column 22,
Line 13, please amend claim 7, as follows:
7. A method for diagnosing liver function, comprising administering to a subject a compound labelled with $^{13}$C at least at one specific position selected from the group consisting of the following (a) to (f):
(a) galactose, glucose or xylose labelled with $^{13}$C at least at one specific position or a starch composed of glucose units labelled with $^{13}$C at least at one specific position;
(b) a polar amino acid excluding tyrosine, heterocyclic amino acid, isoleucine or valine labelled with $^{13}$C at least at one specific position;
(c) a carboxylic acid constituting the glycolytic pathway or the citric acid cycle, labelled with $^{13}$C at least at one specific position
(d) a fatty acid labelled with $^{13}$C at least at one specific position;
(e) a glyceride labelled with $^{13}$C at least at one specific position; and

UNITED STATES PATENT AND TRADEMARK OFFICE
CERTIFICATE OF CORRECTION

PATENT NO. : 6,071,245
DATED : October 1, 1998
INVENTOR(S) : Tadashi Kohno et al.

It is certified that error appears in the above-identified patent and that said Letters Patent is hereby corrected as shown below:

Column 22 (cont'd),
(f) glycerol labelled with $^{13}C$ at least at one specific position; measuring $^{13}C$ levels in the exhaled $CO_2$ for a specific period of time and comparing the degree of increase of $^{13}C$ level with that in healthy individuals.

Signed and Sealed this

First Day of June, 2004

JON W. DUDAS
*Acting Director of the United States Patent and Trademark Office*